(12) United States Patent
Lee et al.

(10) Patent No.: US 12,133,523 B2
(45) Date of Patent: *Nov. 5, 2024

(54) ANTI-FREEZING COMPOSITION COMPRISING SELF-ASSEMBLY COMPOUND

(71) Applicants: Korea University Research and Business Foundation, Seoul (KR); GWANGJU INSTITUTE OF SCIENCE AND TECHNOLOGY, Gwangju (KR)

(72) Inventors: Eun Ji Lee, Seoul (KR); Chang Whan Lee, Seoul (KR); Dong June Ahn, Seoul (KR); In Hye Kim, Gunsan-si (KR); Ha Yeon Kim, Gyeongsan-si (KR); Ye Dam Lee, Seoul (KR)

(73) Assignees: Korea University Research and Business Foundation, Seoul (KR); GWANGJU INSTITUTE OF SCIENCE AND TECHNOLOGY, Gwangju (KR)

(*) Notice: Subject to any disclaimer, the term of this patent is extended or adjusted under 35 U.S.C. 154(b) by 849 days.

This patent is subject to a terminal disclaimer.

(21) Appl. No.: 16/973,494

(22) PCT Filed: Dec. 12, 2019

(86) PCT No.: PCT/KR2019/017575
§ 371 (c)(1),
(2) Date: Dec. 9, 2020

(87) PCT Pub. No.: WO2021/112320
PCT Pub. Date: Jun. 10, 2021

(65) Prior Publication Data
US 2021/0378234 A1 Dec. 9, 2021

(30) Foreign Application Priority Data
Dec. 4, 2019 (KR) .................. 10-2019-0160221

(51) Int. Cl.
*A01N 1/02* (2006.01)
*A23L 3/3526* (2006.01)
*A23L 3/3535* (2006.01)

(52) U.S. Cl.
CPC .......... *A01N 1/0221* (2013.01); *A23L 3/3526* (2013.01); *A23L 3/3535* (2013.01)

(58) Field of Classification Search
None
See application file for complete search history.

(56) References Cited

U.S. PATENT DOCUMENTS 11,697,637 B2 * 7/2023 Lee ...................... A01N 1/0221
548/469
2018/0153194 A1 6/2018 Kawahara et al.

FOREIGN PATENT DOCUMENTS

| EP | 3 119 800 B1 | 2/2018 |
| JP | 2008-521879 A | 6/2008 |
| JP | 2017-512829 A | 5/2017 |
| JP | 2018-538359 A | 12/2018 |
| KR | 10-1396925 B1 | 5/2014 |
| KR | 10-2018-0084782 A | 7/2018 |
| WO | 2012/023486 A1 | 2/2012 |
| WO | 2016/178426 A1 | 11/2016 |

OTHER PUBLICATIONS

Marchesan et al. (Molecules 2015, 20, 19775-19788) (Year: 2015).*
Jaradat et al. (International Journal of Peptide Research and Therapeutics (2019) 25:1095-1102) (Year: 2019).*
Office Action dated Apr. 19, 2022 issued by the Japanese Patent Office in Japanese Application No. 2020-569008.

* cited by examiner

*Primary Examiner* — Sergio Coffa
(74) *Attorney, Agent, or Firm* — Sughrue Mion, PLLC

(57) ABSTRACT

The present invention provides a composition for freezing control, a composition for freezing a cell, and a composition for freezing a food, which include a compound in which 2 to 5 amino acids, for example, 2, 3, 4, or 5 amino acids are connected to fluorenylmethyloxycarbony (Fmoc) through peptide bonding.

1 Claim, 16 Drawing Sheets

[FIG. 1]
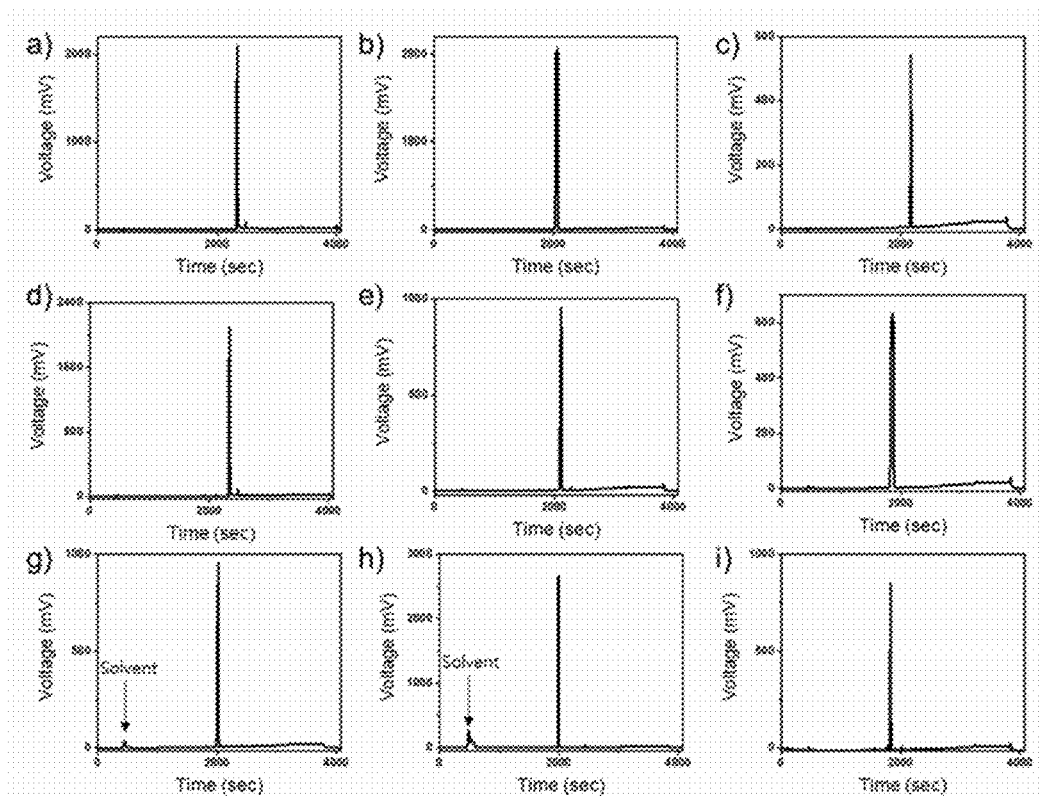

[FIG. 2]
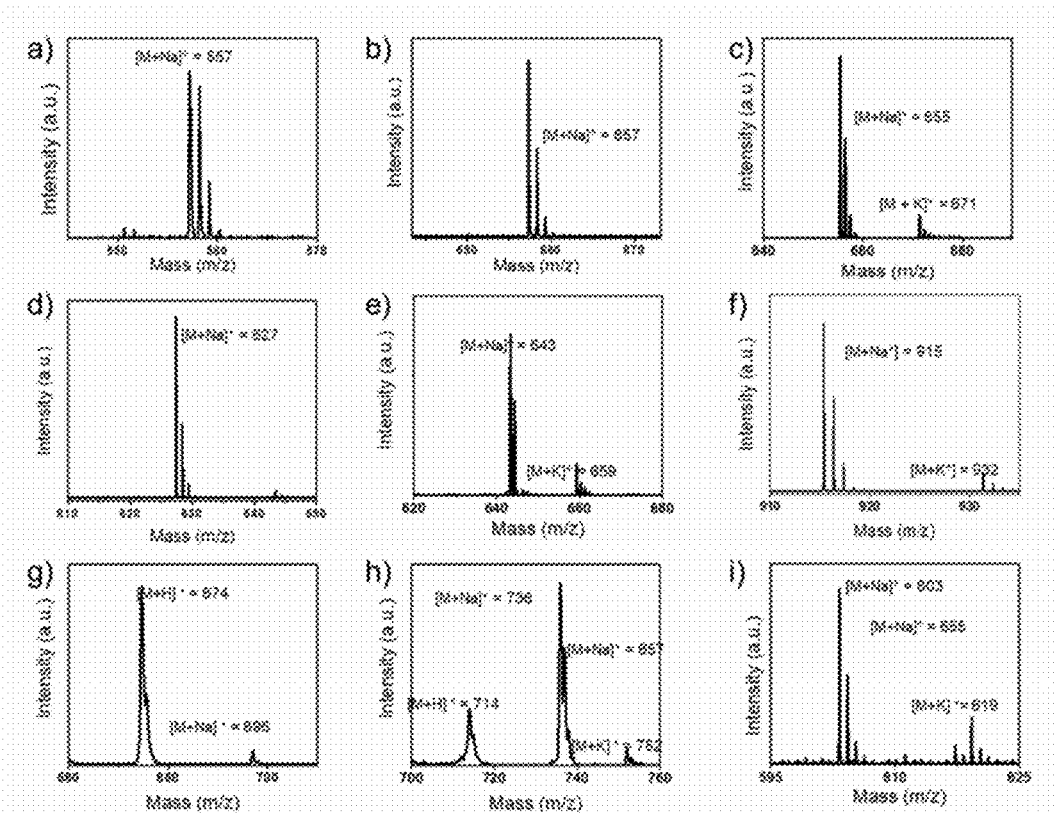
[FIG. 3]
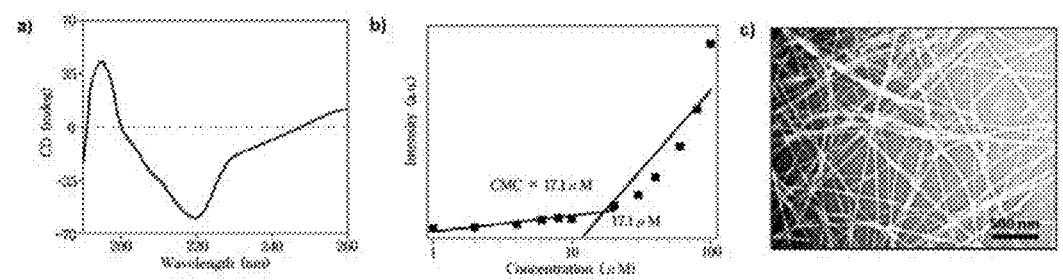

[FIG. 4]
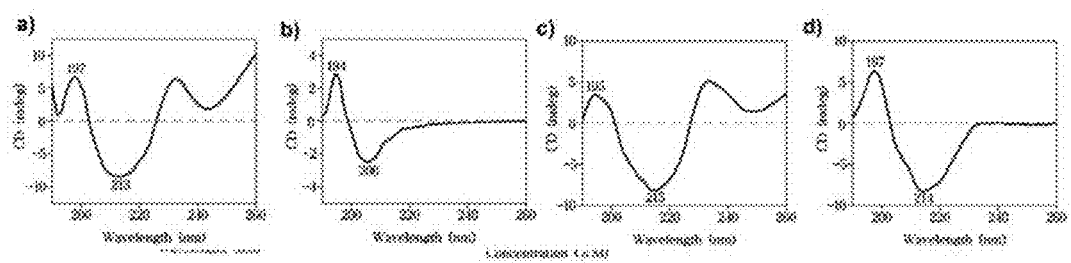
[FIG. 5]
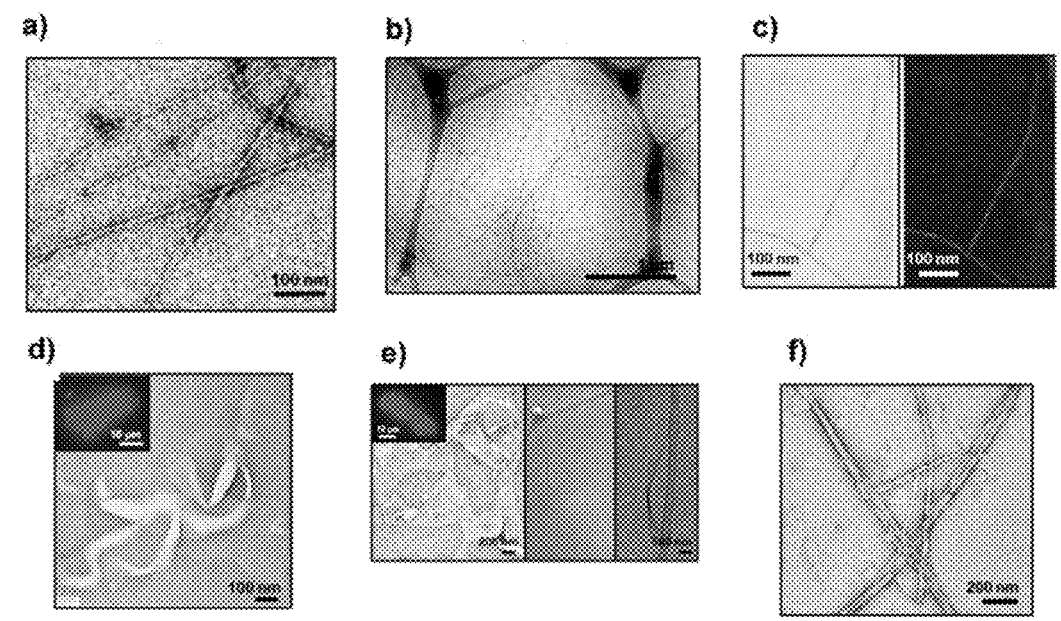

[FIG. 6]
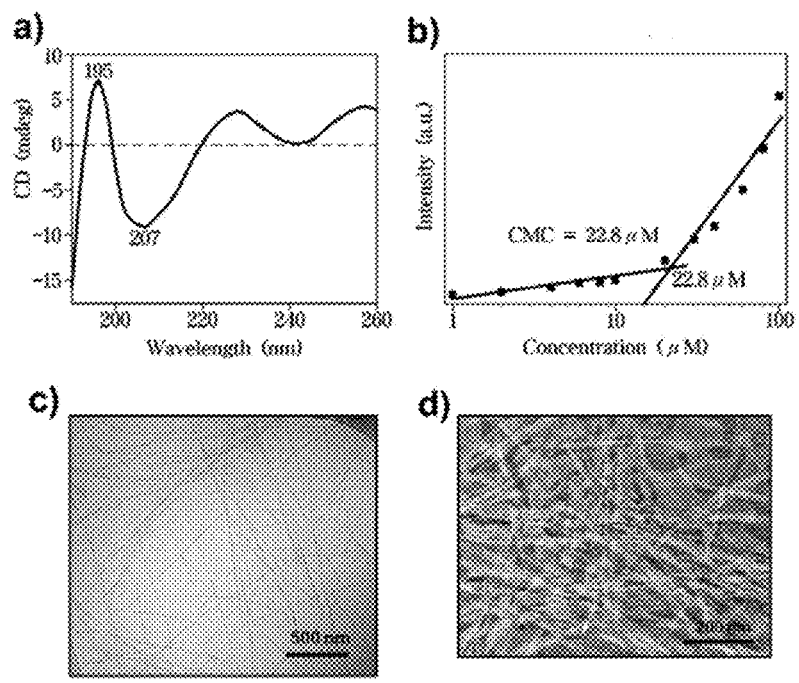
[FIG. 7]
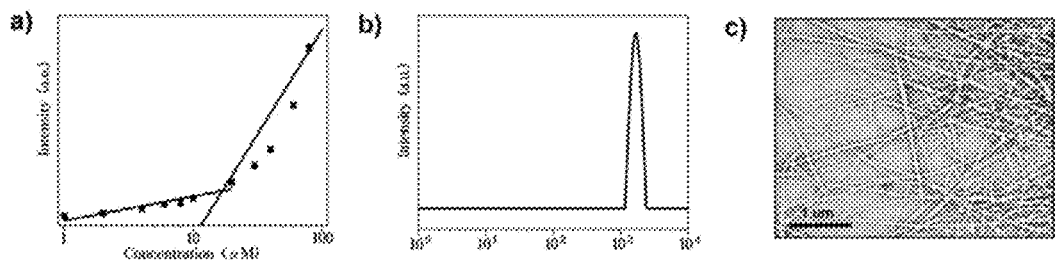

[FIG. 8]
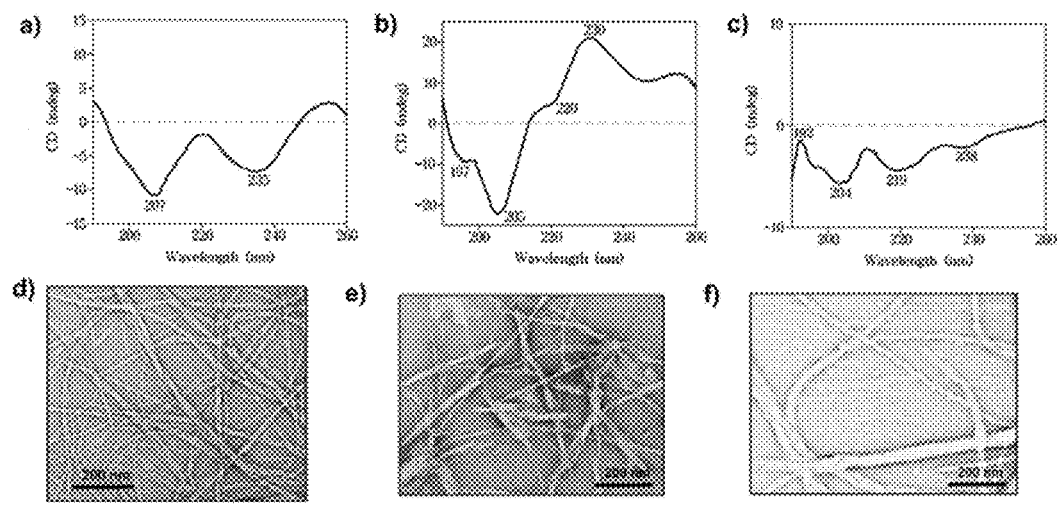
[FIG. 9]
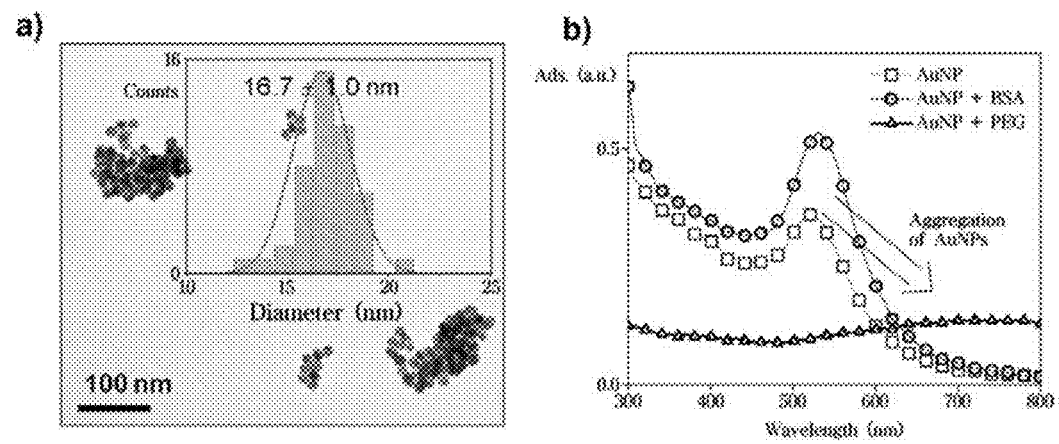

[FIG. 10]
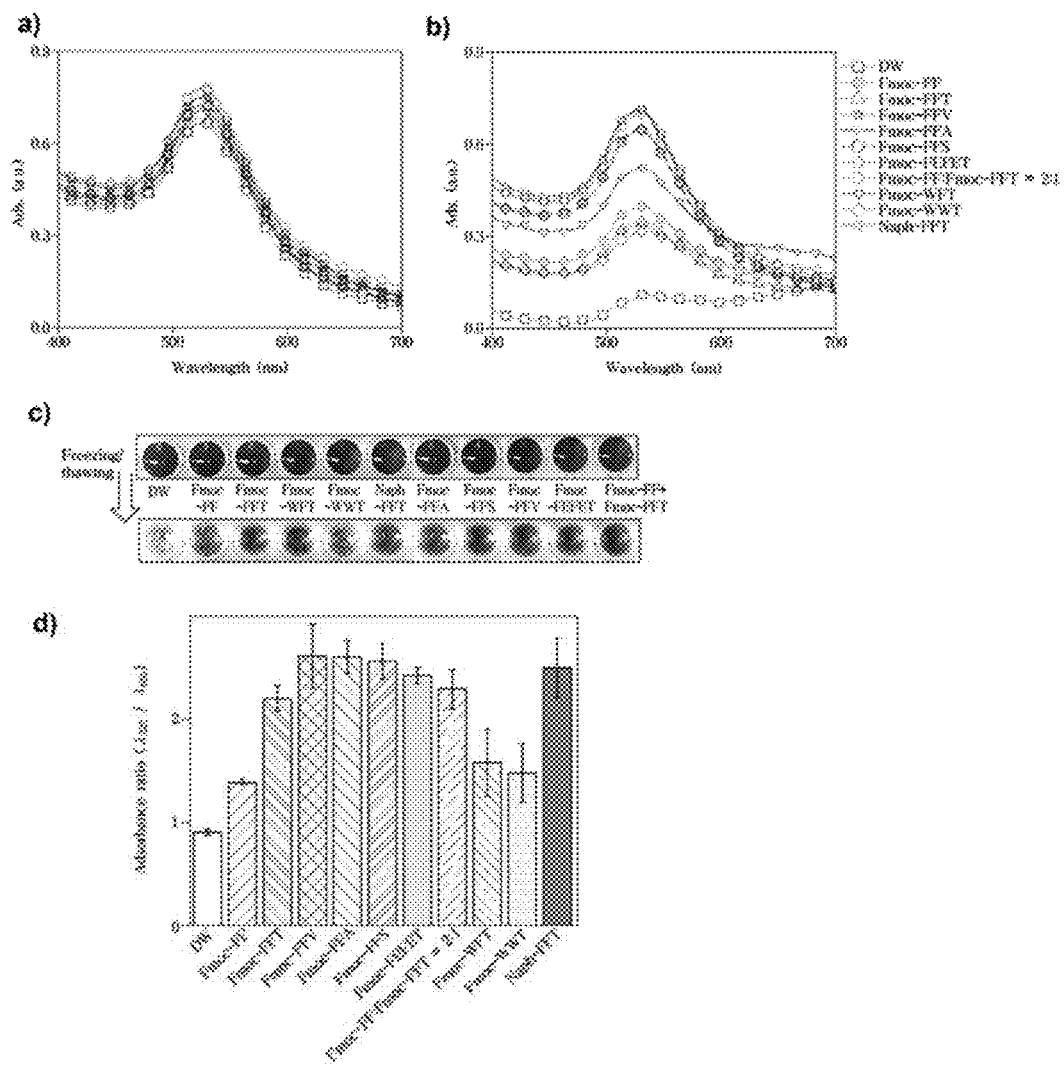

[FIG. 11]
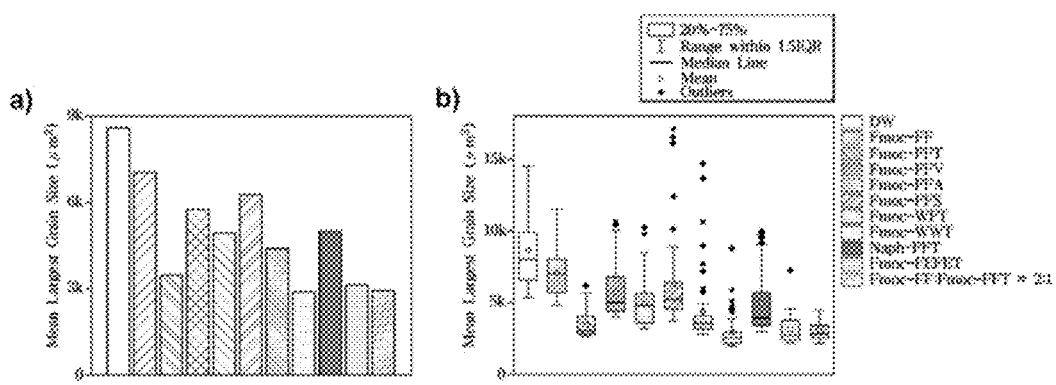

[FIG. 12]
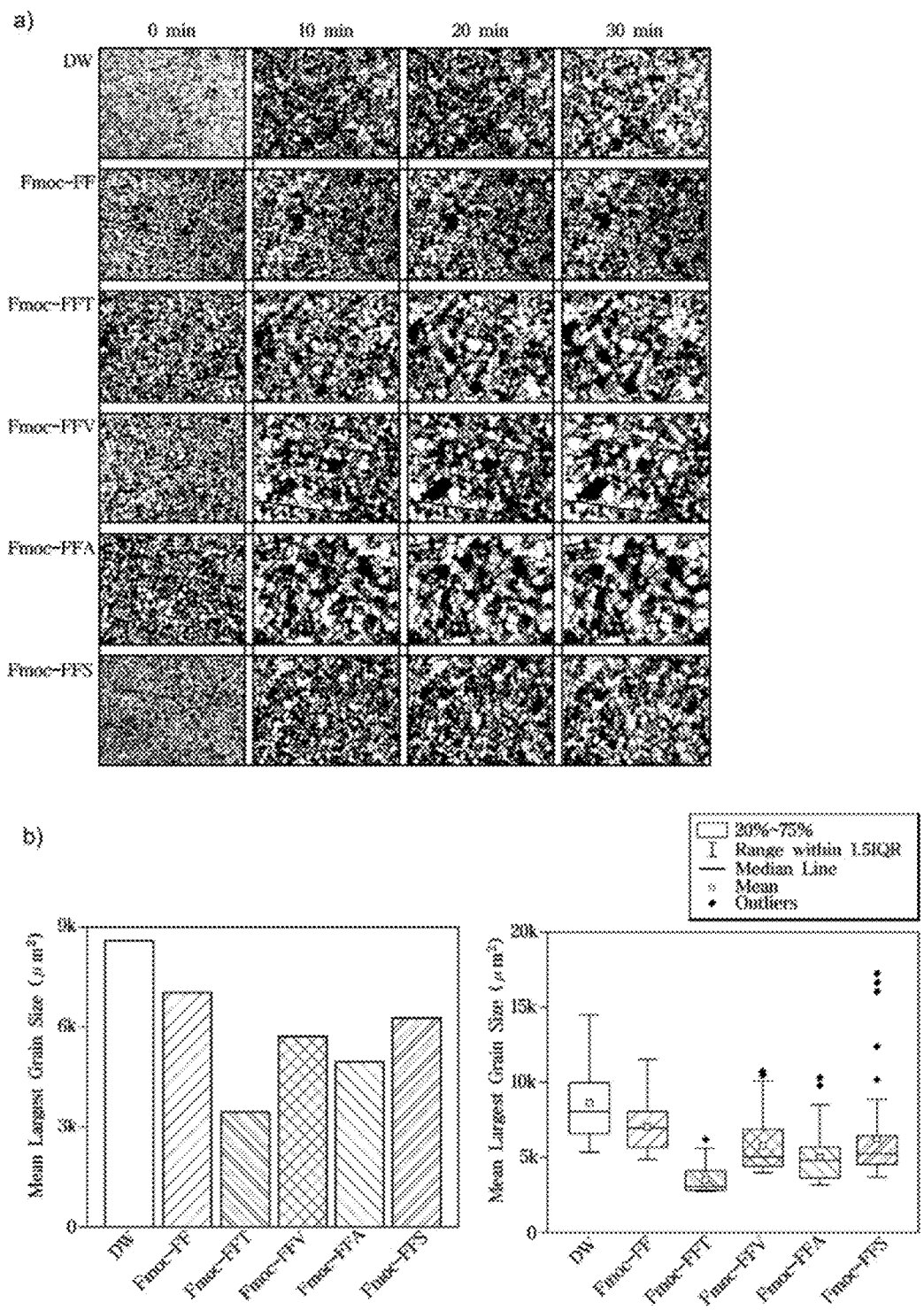

[FIG. 13]
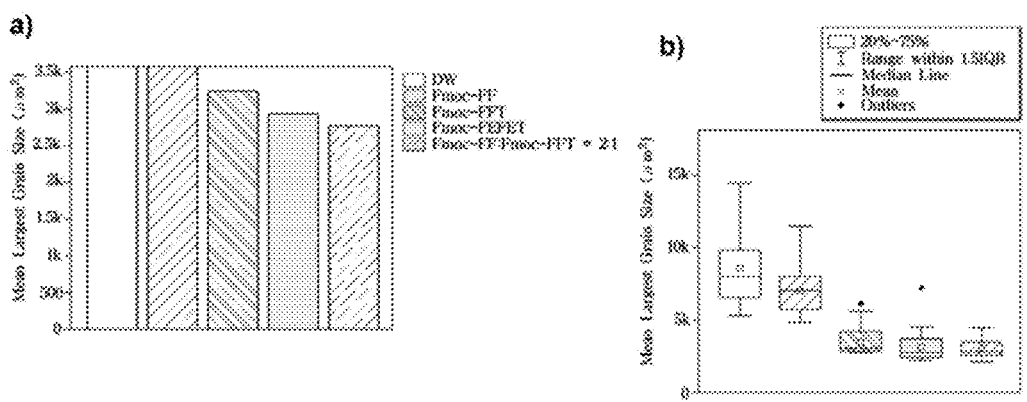

[FIG. 14]
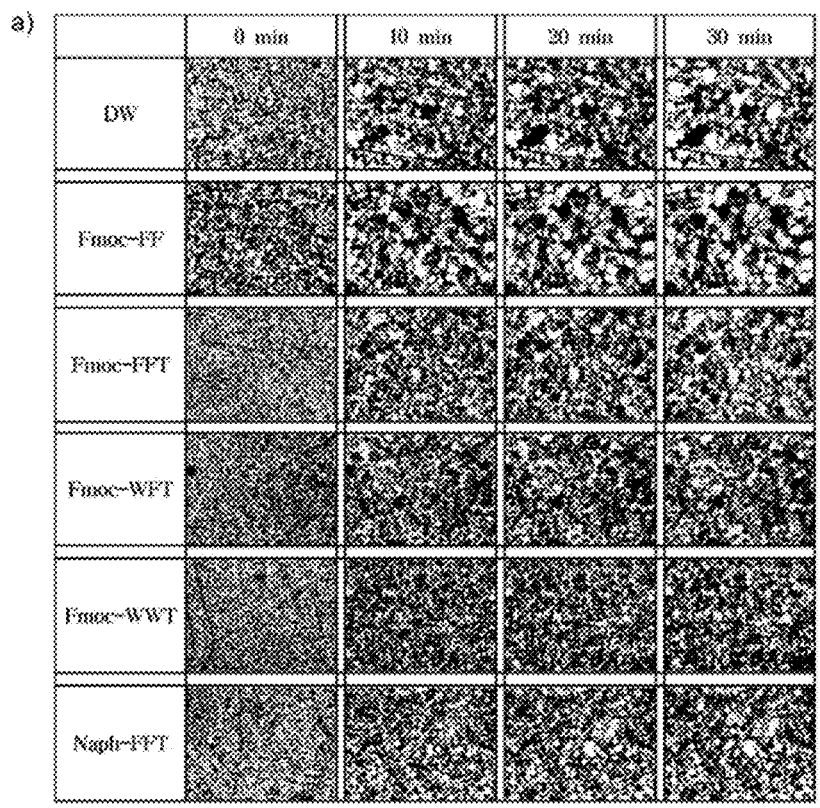
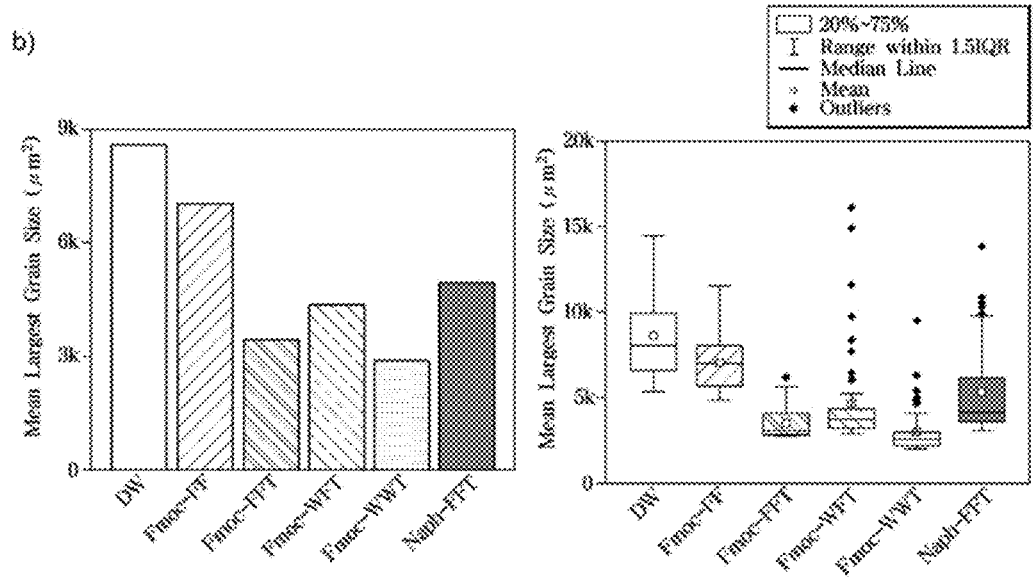

[FIG. 15]
a)
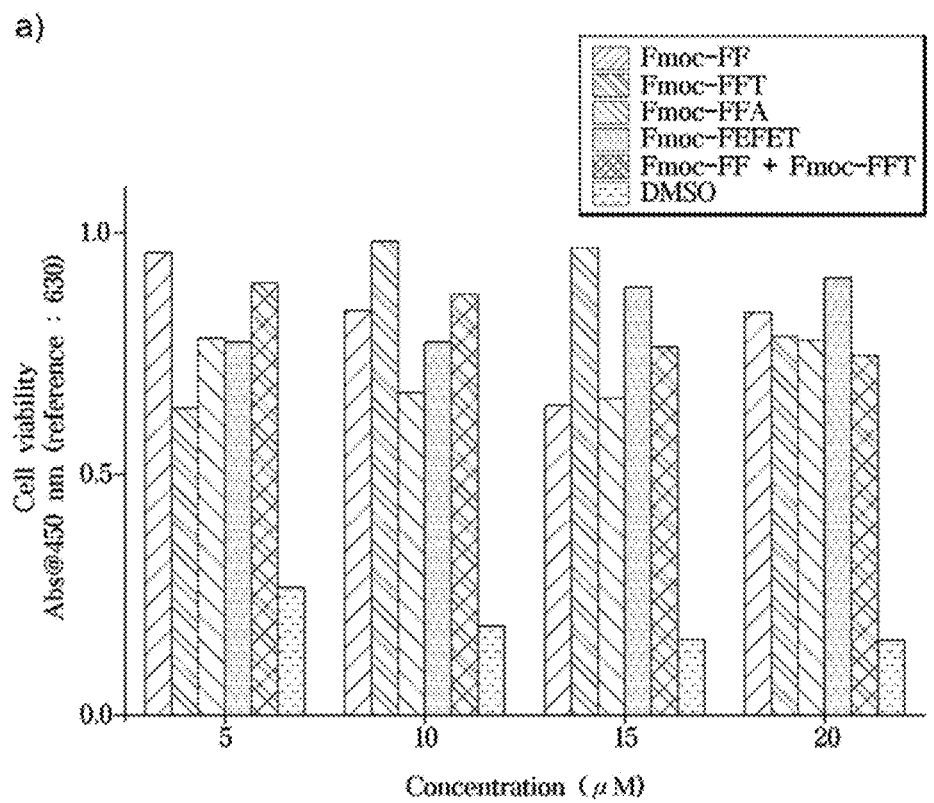
b)
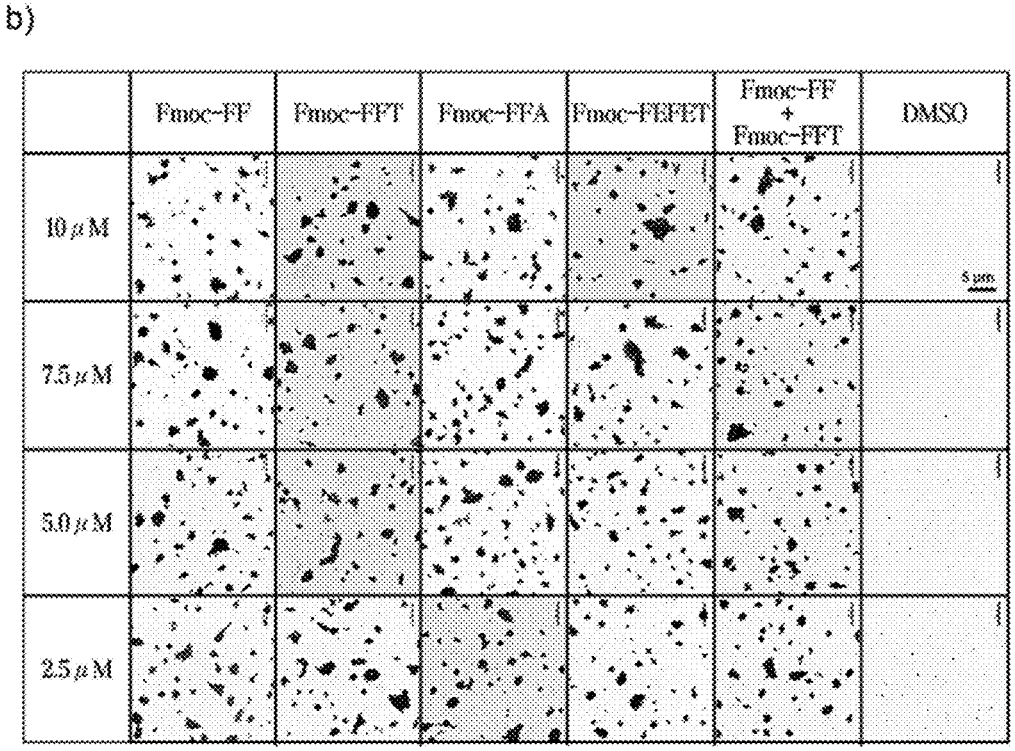

[FIG. 16]
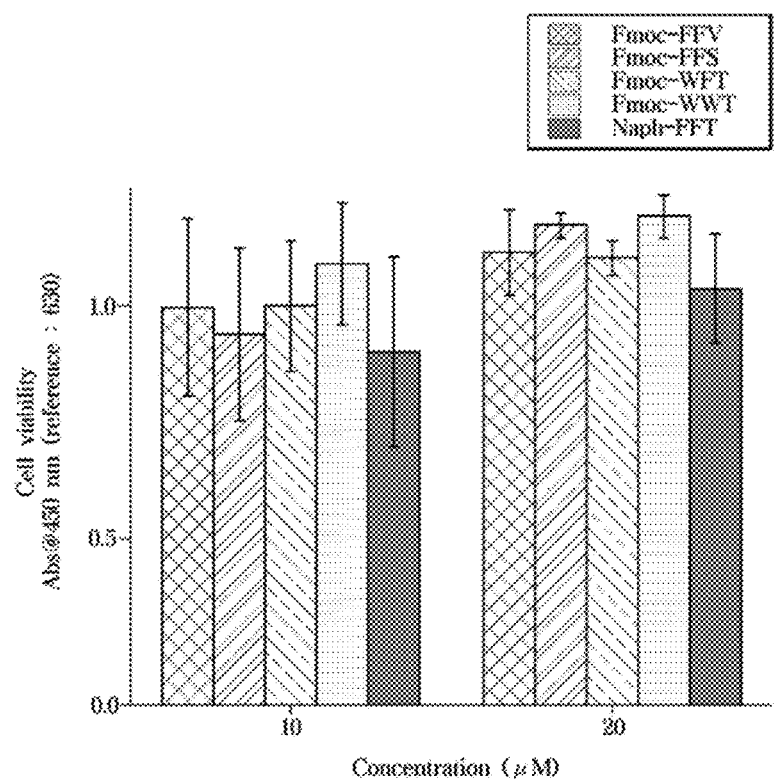

[FIG. 17]
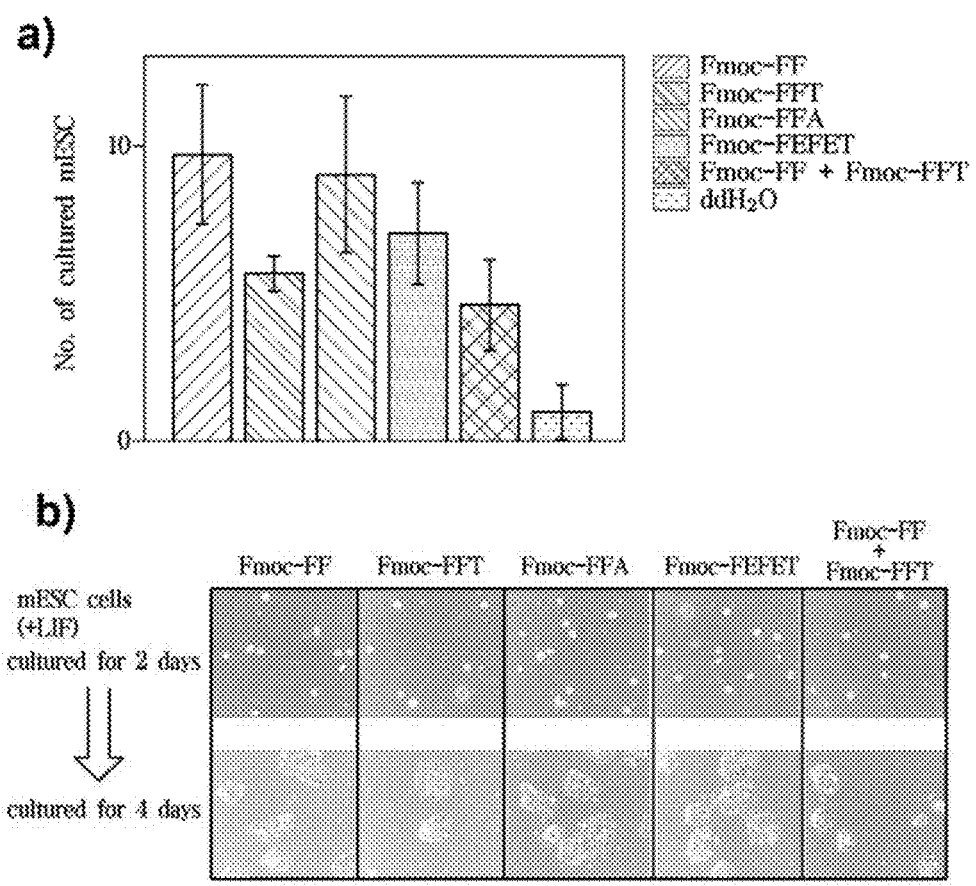

[FIG. 18]
a)
| | Fmoc-FF | Fmoc-FFT | Fmoc-FFA | Fmoc-FEFET | Fmoc-FF + Fmoc-FFT |
|---|---|---|---|---|---|
| 0.005mM | | | | | |
| 0.01mM | | | | | |
| 0.05mM | | | | | |
| 0.1mM | | | | | |
[FIG. 19]
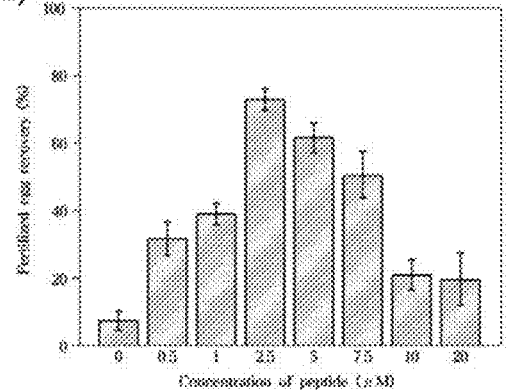

[FIG. 20]
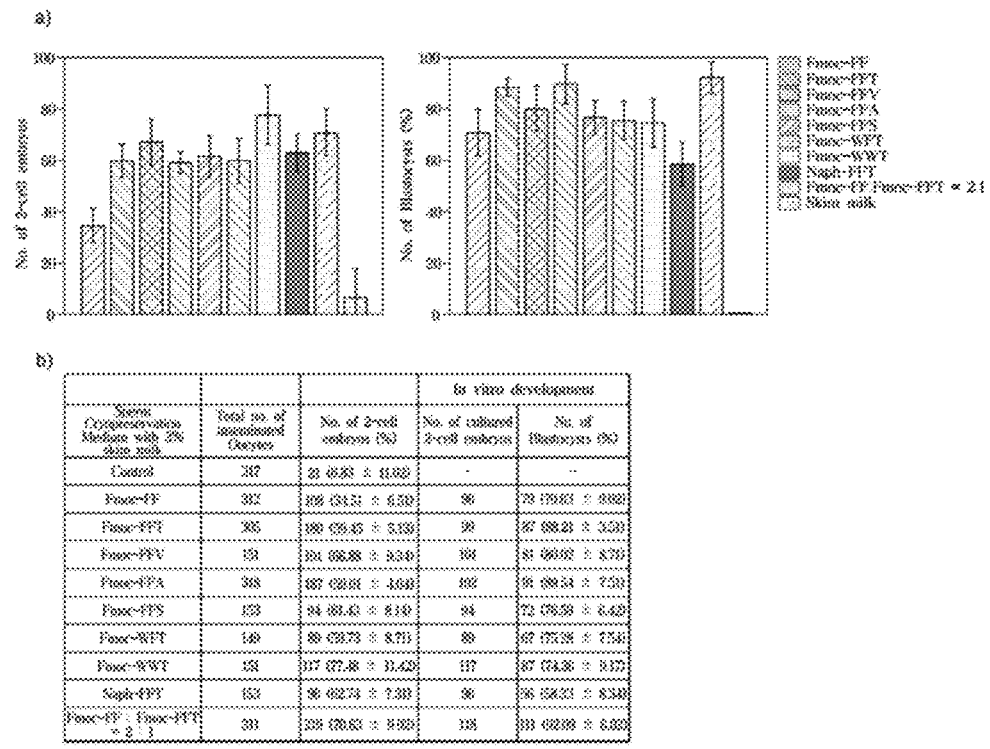
[FIG. 21]

[FIG. 22]
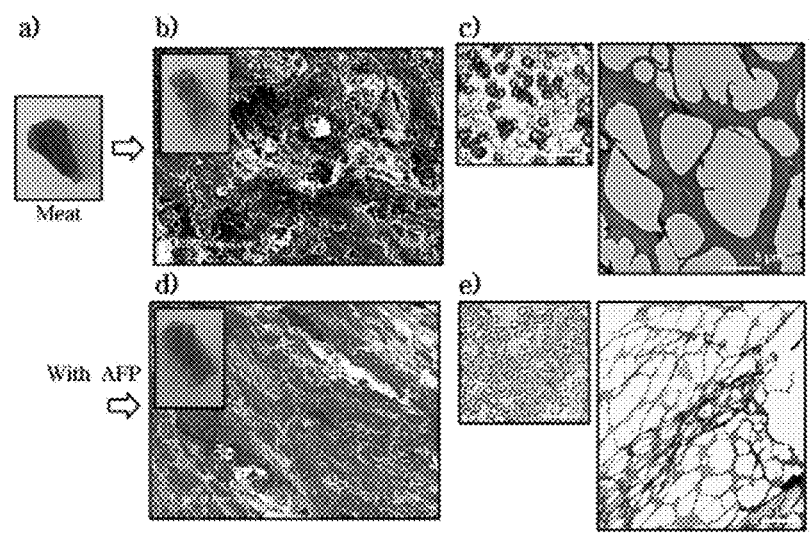

ANTI-FREEZING COMPOSITION COMPRISING SELF-ASSEMBLY COMPOUND

STATEMENT OF JOINT RESEARCH AGREEMENT

The subject matter of the present application was made as a result of a joint research agreement within the meaning of 35 U.S.C. §§ 100(h) and 102(c) and 37 C.F.R. § 1.9(e) between KOREA UNIVERSITY RESEARCH AND BUSINESS FOUNDATION and GWANGJU INSTITUTE OF SCIENCE AND TECHNOLOGY.

CROSS REFERENCE TO RELATED APPLICATIONS

This application is a National Stage of International Application No. PCT/KR2019/017575 filed Dec. 12, 2019, claiming priority based on Korean Patent Application No. 10-2019-0160221 filed Dec. 4, 2019.

TECHNICAL FIELD

The present invention relates to an anti-freezing composition comprising a self-assembled compound.

BACKGROUND ART

A cryoprotective agent (CPA) is a compound capable of reducing ice crystal formation or inhibiting the ice crystal formation in a solution exposed to a temperature below zero (0)° C. when present in the solution. Usually, small molecules, synthetic polymers, and cryoprotective proteins are used as the CPA.

Organ transplantation is the best therapy for end-stage organ failure in terms of a survival rate, quality of life, and cost effectiveness. Unfortunately, there is a long time gap between supply and demand of organ transplants, which is one of important medical barriers that make patients in need of the organ transplants live hard during a long period of waiting time. One of the reasons for the lack of supply of the organs is due to an absence of reliable preservation method.

In order to properly preserve the harvested organ, it is necessary to wash the organ with a preservation solution to remove blood, and stabilize the organ. Even after stabilizing the organ in the preservation solution, an available time for assignment, transport, and transplantation of the organ after removal from a donor is typically limited to 6 to 12 hours. Due to such a short length of time, there is a limitation that most of the harvested organs will be transplanted to local patients, and due to the limitation of travel time, the chance of organ transplantation for remote patients is significantly reduced. As a result of such a shortage of clinically available organs, and although the sale of human organs is prohibited in almost every country, illegal organ transactions and human trafficking have been increased.

Current CPAs used for storage of the organ generally include in particular ethylene glycol, 1,2-propanediol, dimethyl sulfoxide, formamide, glycerol, sucrose, lactose or D-mannitol. In order to reduce or inhibit ice crystal growth (i.e., ice recrystallization) at a temperature required for storage of the organ, an effective concentration of the CPAs should be very high usually 60% or more. It is known that, at such a high concentration, these compounds may exhibit toxic to tissues that are trying to be preserved by the same, and mass removal of the CPAs upon warming prior to the transplantation may result in irreversible cell death.

As other CPAs used to reduce or inhibit ice crystal formation, there are synthetic polymers and cryoprotective proteins. Similar to the CPA described above, each of them has their own drawbacks. For example, anti-freeze proteins (AFPs) that exist in the natural world, such as proteins isolated from fishes, plants or insects, are highly effective in preventing ice formation, but currently available cryoprotective proteins have low purity and high production costs, such that they are considered to be inefficient for use in the industry.

Meanwhile, chemical cryoprotectants, for example, dimethyl sulfoxide (DMSO) are known not only to cause side effects such as fever or tickling, but also to exhibit biotoxicity, for example, deteriorating the brain or acting as a neurotoxin, etc. Therefore, such a chemical cryoprotectant has a disadvantage that it is difficult to use when freezing cells, tissues, organs, foods and the like.

SUMMARY OF INVENTION

Problems to be Solved by Invention

It is an object of the present invention to provide a material having excellent freezing control ability, while having low cytotoxicity and biotoxicity.

In addition, another object of the present invention is to develop a material capable of inhibiting recrystallization of ice or an increase in a diameter of ice crystals.

Further, another object of the present invention is to provide a composition for freezing control, a composition for freezing a cell, and a composition for freezing a food including the above material.

Means for Solving Problems

1. A composition for controlling freezing, including a compound represented by Formula 1 or Formula 2 below:

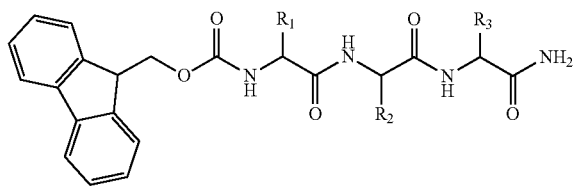

[Formula 1]

-continued

[Formula 2]

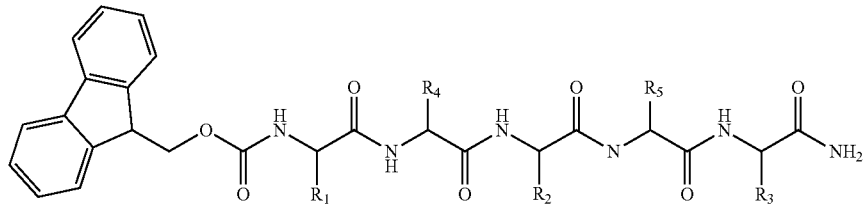

In Formula 1 or 2 above,
$R_1$ and $R_2$ are each independently

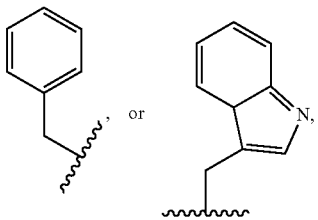 [SMILES: *Cc1ccccc1 ; *CC1=CN=C2C=CC=CC12]

$R_3$ is

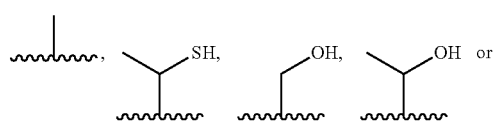

2. The composition for controlling freezing according to item 1, wherein the compound is self-assembled to form a fibril or sheet-shaped structure.

3. The composition for controlling freezing according to item 1, further including a compound represented by Formula 3 below, wherein the composition includes a compound represented by Formula 1 above, and the compound represented by Formula 3 and the compound represented by Formula 1 are included in a ratio of 2:1 (mole:mole):

[Formula 3]

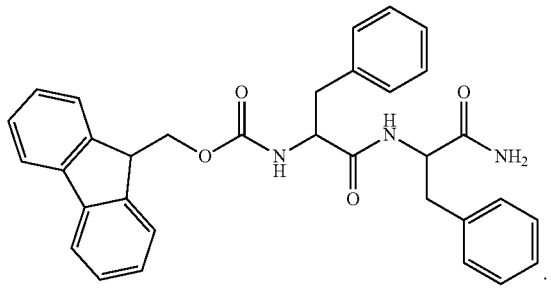

4. The composition for controlling freezing according to item 3, wherein, in Formula 1 above, $R_1$ and $R_2$ are each independently

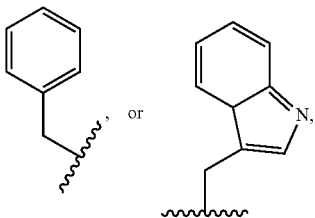 [SMILES: *Cc1ccccc1 ; *CC1=CN=C2C=CC=CC12]

and $R_3$ is.

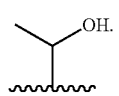

5. The composition for controlling freezing according to item 1, including at least one of the following compounds:

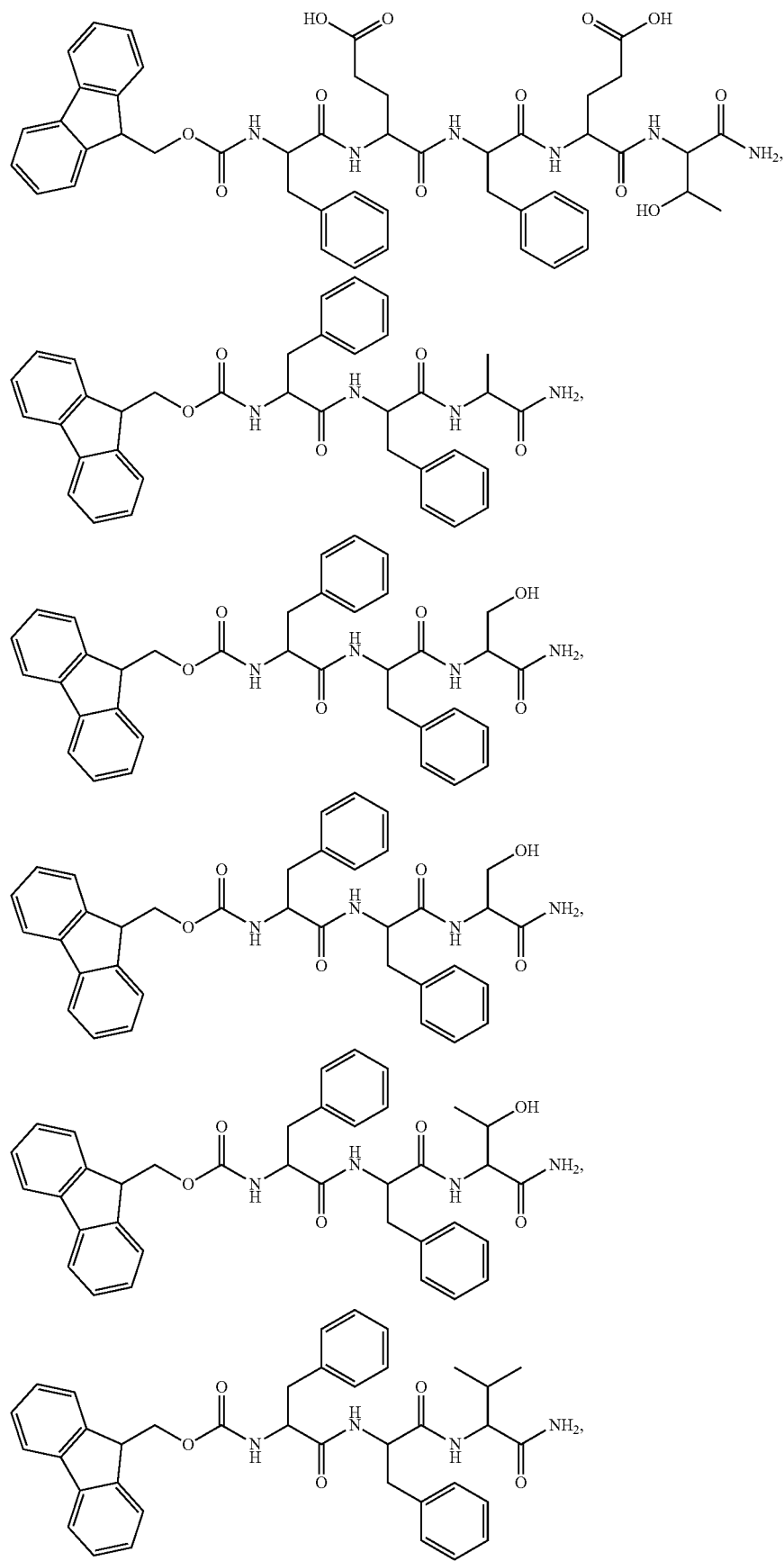

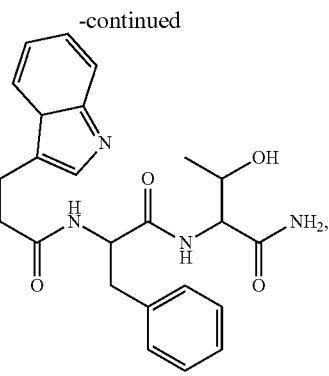
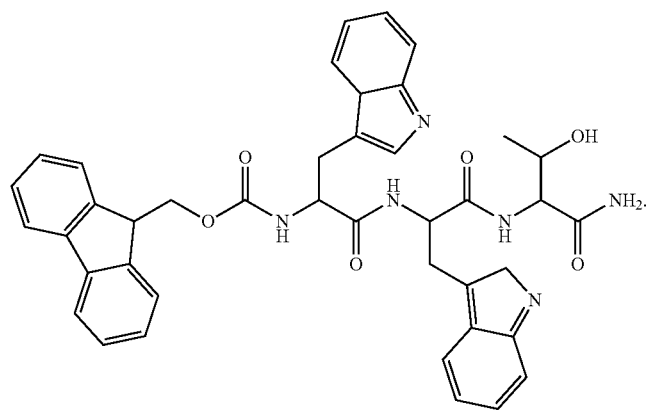
6. A composition for freezing a cell, including a compound represented by Formula 1 or Formula 2 below:
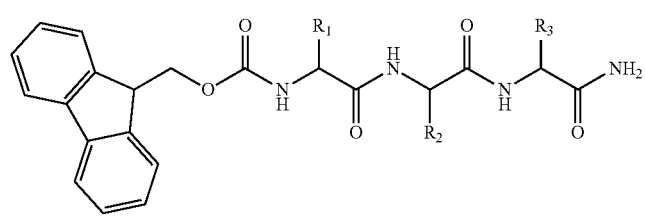
[Formula 1]
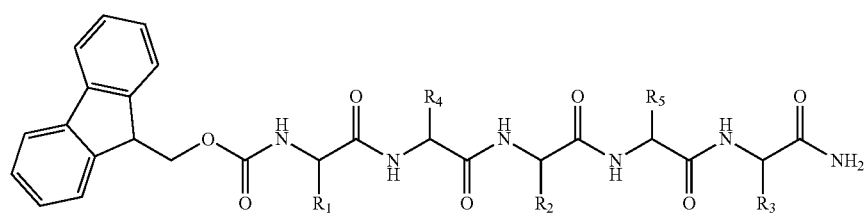
[Formula 2]
In Formula 1 or 2 above, In Formula 1 or 2 above,
$R_1$ and $R_2$ are each independently

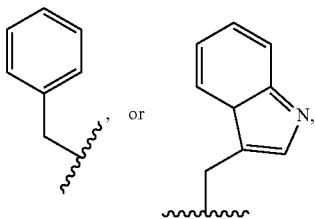 [SMILES: *Cc1ccccc1 ; *CC1=CN=C2C=CC=CC12], or $R_3$ is

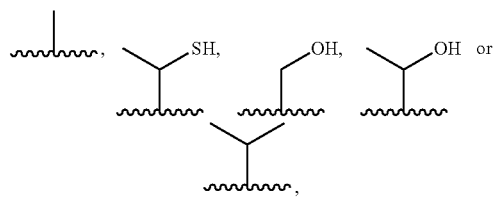, and
$R_4$ and $R_5$ are each independently

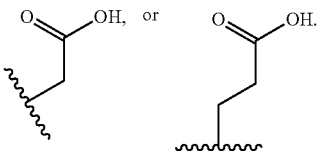 [SMILES: *CC(=O)O ; *CCC(=O)O].

7. The composition for freezing a cell according to item 6, wherein the compound is self-assembled to form a fibril or sheet-shaped structure.

8. The composition for freezing a cell according to item 6, further including a compound represented by Formula 3 below, wherein the composition includes a compound represented by Formula 1 above, and the compound represented by Formula 3 and the compound represented by Formula 1 are included in a ratio of 2:1 (mole:mole):

[Formula 3]

9. The composition for freezing a cell according to item, wherein, in Formula 1 above, $R_1$ and $R_2$ are each independently

, or

and $R_3$

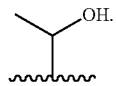 [SMILES: *C(C)O]

10. The composition for freezing a cell according to item 6, including at least one of the following compounds:

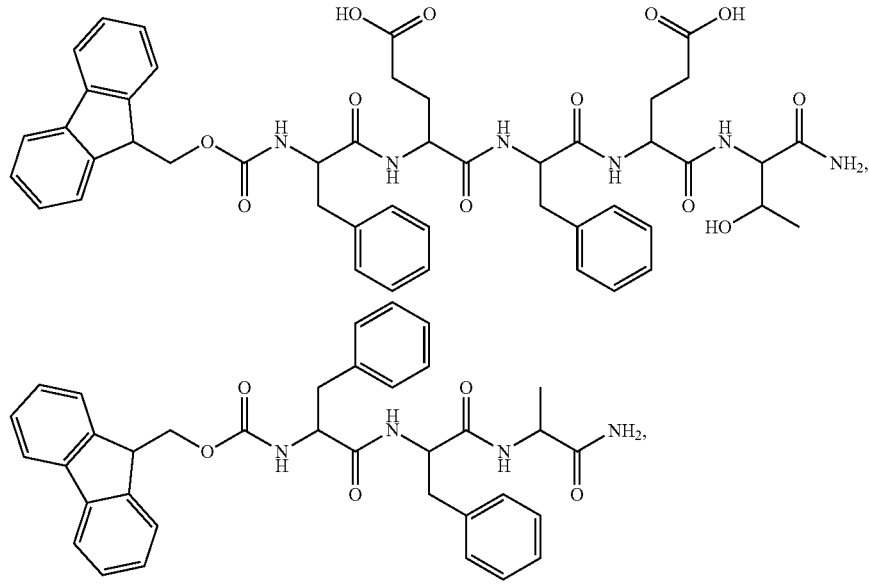

-continued
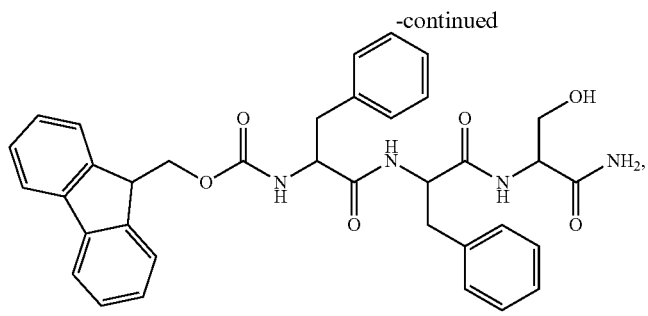
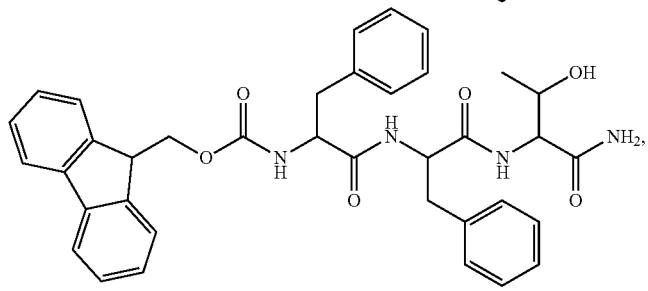
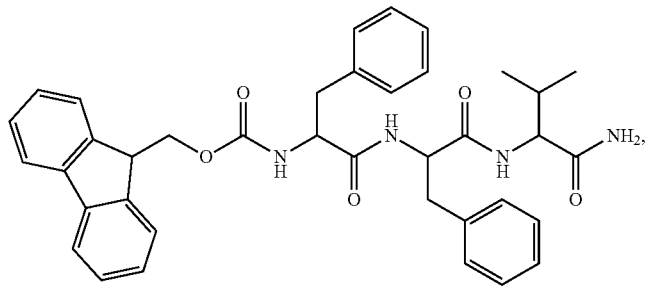
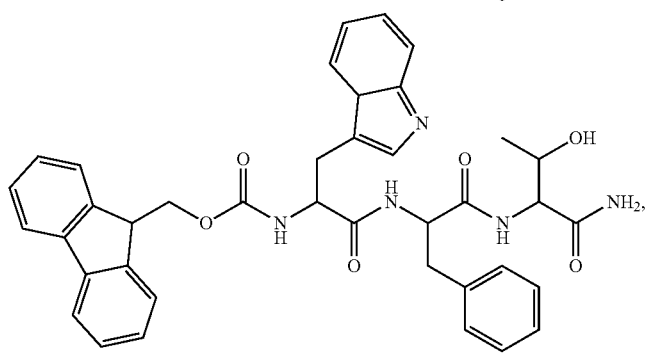
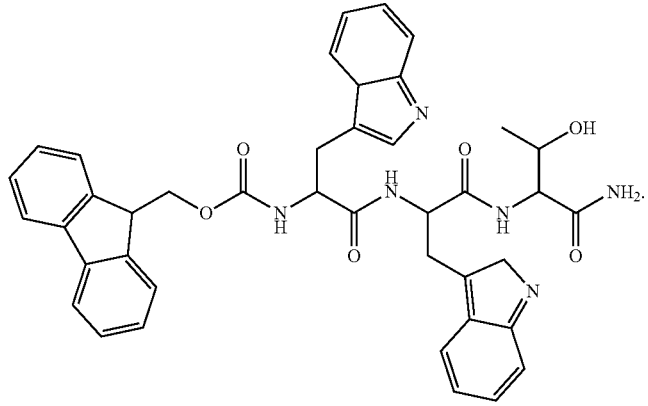
11. The composition for freezing a cell according to item 6, wherein the cells are sperms, eggs, epithelial cells, nerve cells, epidermal cells, keratinocytes, hematopoietic cells, melanocytes, chondrocytes, B cells, T cells, red blood cells, macrophages, monocytes, fibroblasts, muscle cells, embryonic stem cells, mesenchymal stem cells, or adult stem cells.

12. A composition for freezing a food, including a compound represented by Formula 1 or Formula 2 below:

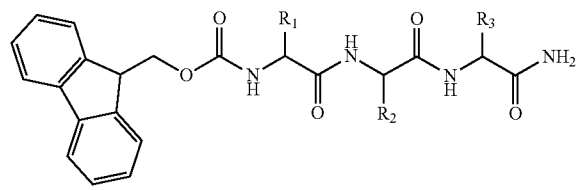

[Formula 1]

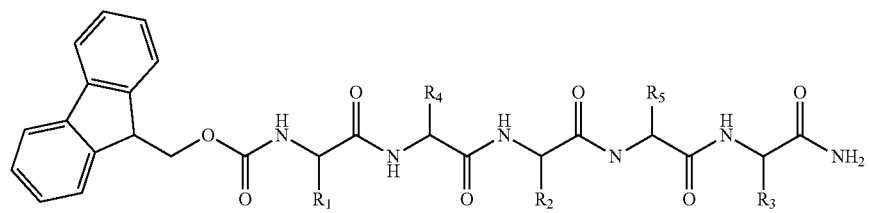

[Formula 2]

In Formula 1 or 2 above,
$R_1$ and $R_2$ are each independently

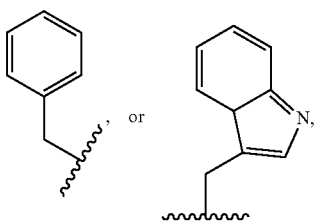 [SMILES: *Cc1ccccc1 ; *CC1=CN=C2C=CC=CC12]

$R_3$ is

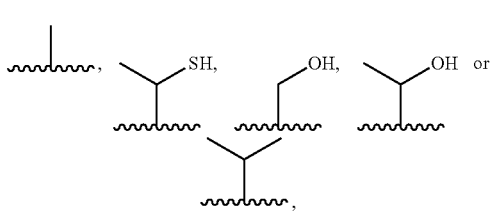

and
$R_4$ and $R_5$ are each independently

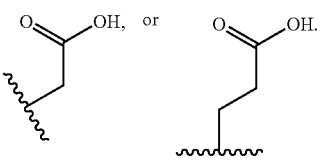 [SMILES: *CC(=O)O ; *CCC(=O)O]

13. The composition for freezing a food according to item 12, wherein the compound is self-assembled to form a fibril or sheet-shaped structure.

14. The composition for freezing a food according to item 12, further including a compound represented by Formula 3 below, wherein the composition includes a compound represented by Formula 1 above, and the compound represented by Formula 3 and the compound represented by Formula 1 are included in a ratio of 2:1 (mole:mole):

[Formula 3]

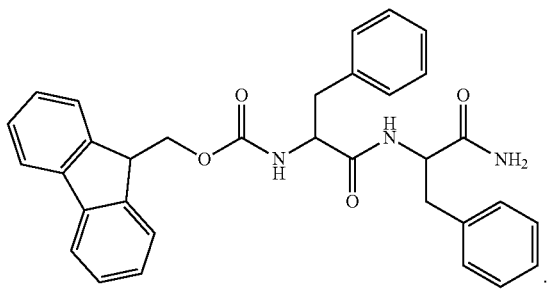

15. The composition for controlling freezing according to item 14, wherein, in Formula above, $R_1$ and $R_2$ are each independently

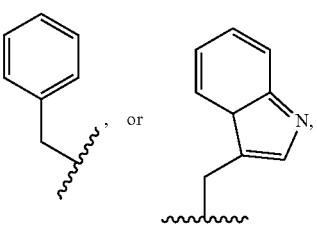 [SMILES: *Cc1ccccc1 ; *CC1=CN=C2C=CC=CC12]

and $R_3$ is

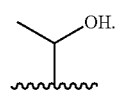

16. The composition for freezing a food according to item 12, including at least one of the following compounds:

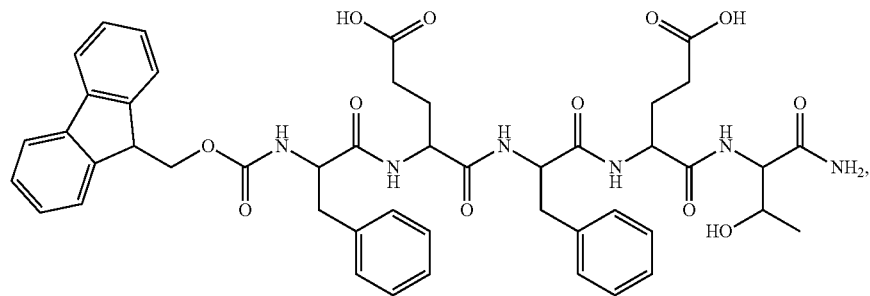
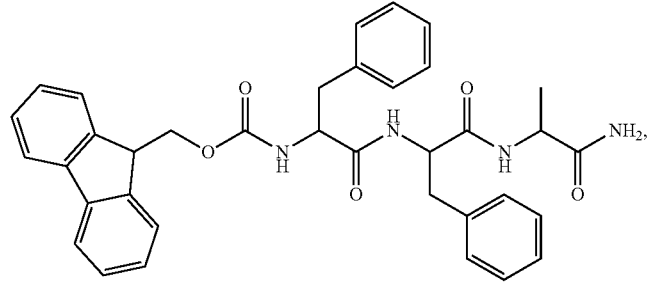
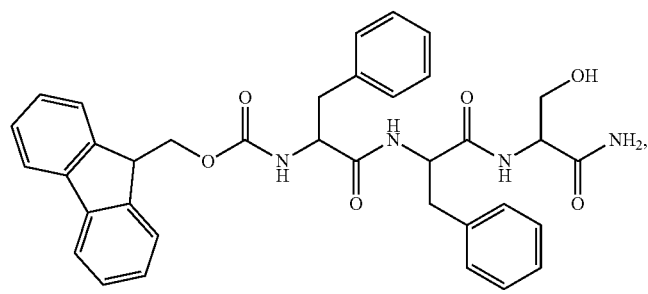
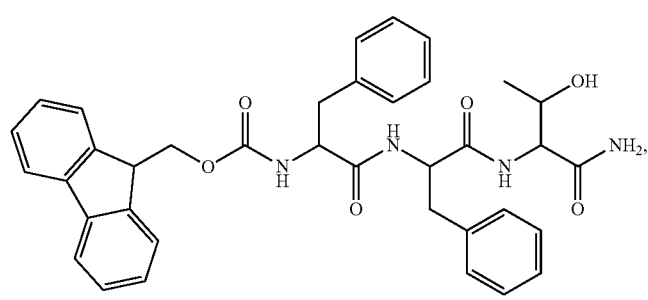
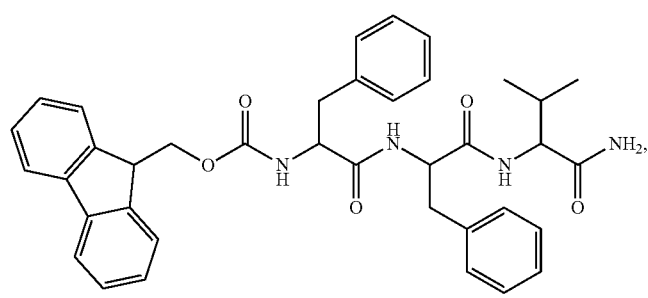

-continued
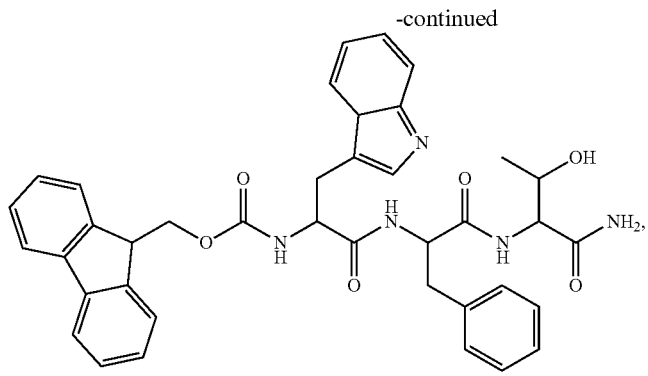
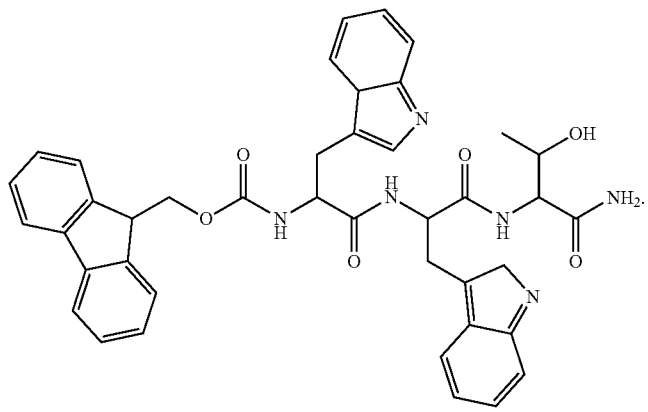
17. A method for controlling freezing, including adding a compound represented by Formula 1 or Formula 2 below to a solvent:
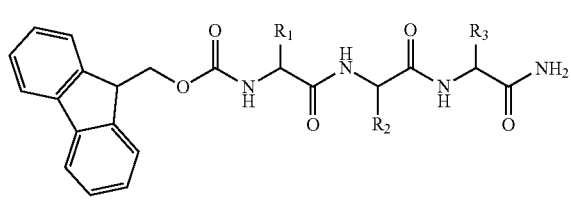
[Formula 1]
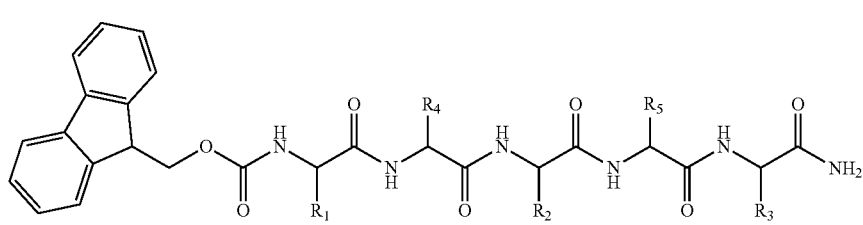
[Formula 2]

In Formula 1 or 2 above,
$R_1$ and $R_2$ are each independently

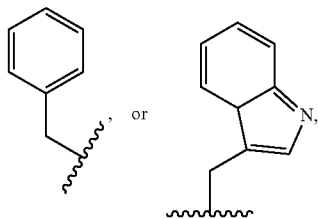 [SMILES: *Cc1ccccc1 ; *CC1=CN=C2C=CC=CC12]

$R_3$ is

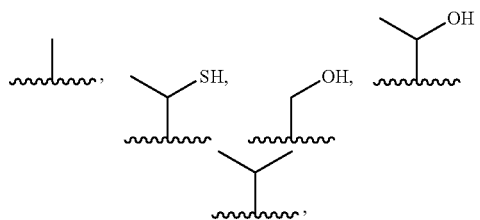

and
$R_4$ and $R_5$ are each independently

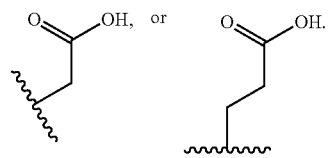 [SMILES: *CC(=O)O ; *CCC(=O)O]

18. A method for cryopreserving a cell including: adding a compound represented by Formula 1 or Formula 2 to the cell for treatment:

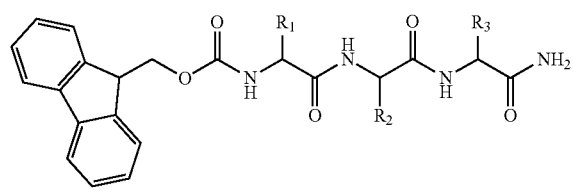

In Formula 1 or 2 above,
$R_1$ and $R_2$ are each independently

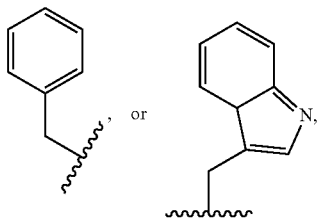 [SMILES: *Cc1ccccc1 ; *CC1=CN=C2C=CC=CC12]

$R_3$ is

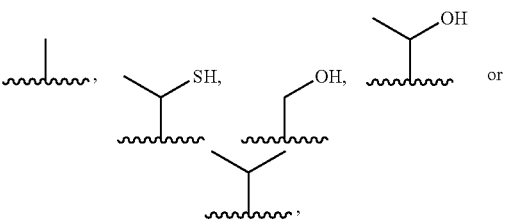

and
$R_4$ and $R_5$ are each independently

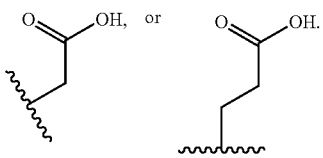 [SMILES: *CC(=O)O ; *CCC(=O)O]

19. A method for cryopreserving a food including: adding a compound represented by Formula 1 or Formula 2 to the food for treatment:

[Formula 1]

[Formula 2]

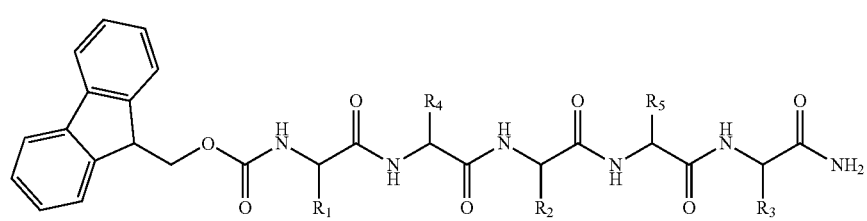

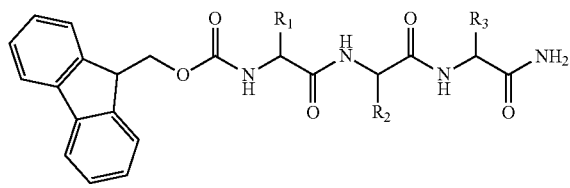

[Formula 1]

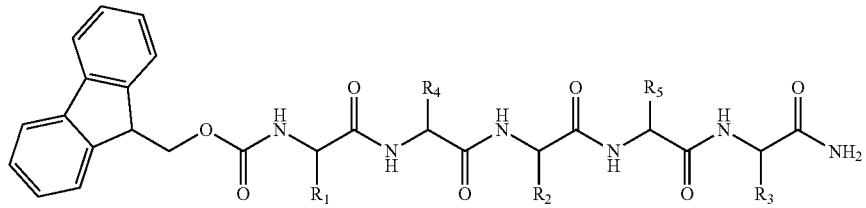

[Formula 2]

In Formula 1 or 2 above,
$R_1$ and $R_2$ are each independently

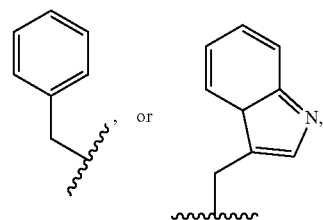 [SMILES: *Cc1ccccc1 ; *CC1=CN=C2C=CC=CC12]

$R_3$ is

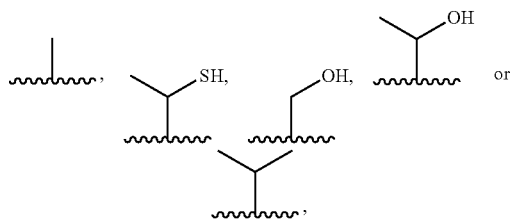

and
$R_4$ and $R_5$ are each independently

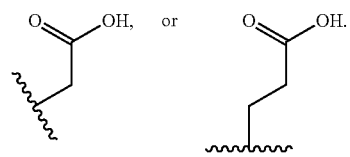

Advantageous Effects

According to the present invention, it is possible to provide a material having excellent freezing control ability, while having low cytotoxicity and biotoxicity.

The freezing control material according to the present invention may inhibit recrystallization of ice or an increase in the diameter of ice crystals.

It is possible to provide a composition for freezing control, a composition for freezing a cell, and a composition for freezing a food including the material according to the present invention.

BRIEF DESCRIPTION OF DRAWINGS

FIG. 1 is HPLC spectra of a) Fmoc-FF, b) Fmoc-FFT, c) Fmoc-FFV, d) Fmoc-FFA, e) Fmoc-FFS, f) Fmoc-FEFET, g) Fmoc-WFT, h) Fmoc-WWT, and i) Naph-FFT.

FIG. 2 is MALDI-TOF/TOF MS spectra of a) Fmoc-FF, b) Fmoc-FFT, c) Fmoc-FFV, d) Fmoc-FFA, e) Fmoc-FFS, f) Fmoc-FEFET, g) Fmoc-WFT, h) Fmoc-WWT, and i) Naph-FFT.

FIG. 3 is diagrams, wherein a) is a CD spectrum illustrating a secondary structure of Fmoc-FF in an aqueous solution, b) is a graph illustrating Fmoc-FF concentration of critical micelle aggregation, and c) is a TEM image of Fmoc-FF.

FIG. 4 is CD spectra of a) Fmoc-FFT, b) Fmoc-FFV, and c) Fmoc-FFA, and Fmoc-FFS in an aqueous solution.

FIG. 5 is images, wherein a) is a TEM image of Fmoc-FFT, b) is a cryogenic-TEM of Fmoc-FFT, and c) is an STEM image of Fmoc-FFT, and d) is a TEM image of Fmoc-FFV (top left, fluorescence microscope), e) is TEM and cryogenic-TEM images of Fmoc-FFA (top left, fluorescence microscope), and f) is a TEM image of Fmoc-FFS in an aqueous solution.

FIG. 6 is diagrams, wherein a) is a CD spectrum illustrating a secondary structure of Fmoc-FEFET in an aqueous solution, b) is a graph illustrating Fmoc-FEFET concentration of critical micelle aggregation, c) is a TEM image of Fmoc-FEFET, and d) is a cryogenic-TEM image of Fmoc-FEFET for illustrating a formation of fibrils.

FIG. 7 is diagrams, wherein a) is a graph illustrating a concentration of a co-assembly structure of Fmoc-FF and Fmoc-FFT at a micelle aggregation threshold, b) is a graph illustrating results of confirming a hydraulic radius of the co-assembly structure of Fmoc-FF and Fmoc-FFT by DLS, and c) is a TEM image of the co-assembled structure of Fmoc-FF and Fmoc-FFT.

FIG. 8 is diagrams, wherein a) is a CD spectrum of Fmoc-WFT, b) is a CD spectrum of Fmoc-WWT, c) is a CD spectrum of Naph-FFT, d) is a TEM image of Fmoc-WFT, e) is a TEM image of Fmoc-WWT, and f) is a TEM image of Naph-FFT.

FIG. 9 is diagrams, wherein a) is a TEM image of a 16.7 nm spectrum of MPA-Au nanoparticles having a diameter of 16.7 nm, and b) is an extinction spectrum after freezing/thawing of MPA-AuNP, MPA-AuNP+2 µM BSA, and MPA-AuNP+2 µM PEG, and freeze-induced assembly may be quantified by the extinction spectrum.

FIG. 10 is graphs illustrating changes in absorption spectra before (a) and after (b) freezing/thawing of self-assembled nanostructures, wherein c) is a photograph taken before and after freezing/thawing of MPA-AuNP solution (350 µL of 300 µM) mixed with each material (50 µL of 0.5 mM) in a microwell dish, and d) is a graph illustrating Au NP aggregation quantified by an absorption rate in c).

FIG. 11 is graphs illustrating results of recrystallizing an ice for 30 minutes and calculating MLGS of the recrystallization domains of all materials from a DFOM image, wherein a) and b) show that ten largest domains in a visible system were selected and measured by averaging.

FIG. 12 is images illustrating IRI activities of Fmoc-FF, Fmoc-FFT, Fmoc-FFV, Fmoc-FFA, and Fmoc-FFS, wherein a) shows DFOM in chronological order for illustrating recrystallization of ice recrystallized for 30 minutes, and b) is graphs illustrating results of calculating MLGS of recrystallization domains of each material using the images from a).

FIG. 13 is graphs illustrating MLGS of a co-assembly of Fmoc-FF, Fmoc-FFT, Fmoc-FEFET, and Fmoc-FF: Fmoc-FFT.

FIG. 14 is images (a) illustrating IRI activities of Fmoc-FF, Fmoc-FFT, Fmoc-WFT, Fmoc-WWT, and Naph-FFT, wherein DFOMs showing ice recrystallization were photographed over time, and ice was recrystallized for 30 minutes, and is graphs (b) illustrating results of calculating MLGS of recrystallization domains of each material using the images from a).

FIG. 15 is a graph (a) illustrating cell viability determined by CCK-analysis of mESC at various sample concentrations, and is images (b) confirmed by crystal violet dye.

FIG. 16 is a graph illustrating cell viability confirmed by CCK-analysis of mESC.

FIG. 17 is a graph (a) illustrating that mESC was cryopreserved with each sample and then thawed at 37° C. to confirm cell viability, which is expressed in a mean+SD format, and is images (b) illustrating for confirming differentiation of mESCs for 4 days after cryopreservation using the sample.

FIG. 18 is a result of confirming differentiation of mESC for 4 days after cryopreservation depending on the concentration of the cryopreservation solution.

FIG. 19 is a table and a graph illustrating results of confirming fertility of frozen/thawed sperm on a co-assembly of Fmoc-FF and Fmoc-FFT.

FIG. 20 is graphs and tables illustrating results of confirming a development of embryo (a) and blastocyst (b) by injecting cryopreserved sperms using the sample.

FIG. 21 is a table illustrating developments of C57BL/6 derived 2-cell embryo in vitro and in vivo.

FIG. 22 is SEM images (b and d), optical microscopes (c, and left of e), and TEM images (c, and right of e) illustrating results of confirming sizes and textures of ice crystals in a case (d, and e) of treating with Fmoc-FFT before freezing beef (a) and a case (b, and c) without treatment, respectively.

MODE FOR CARRYING OUT INVENTION

Hereinafter, the present invention will be described in more detail with reference to the accompanying drawings. However, some embodiment of the present invention, but not limited thereto, are illustrated. In fact, these invention may be practically embodied in various formed and should not be construed to limit the present invention to the embodiments proposed in the present disclosure. Singular forms used in the specification and appended claims may also include plural forms unless otherwise specifically indicated.

In the present disclosure, "antifreeze protein" and "antifreeze protein" or "AFP" may be used interchangeably, and AFPs are found in a variety of animals, plants, fungi and bacteria, and they are known to conjugate to ice crystals to inhibit growth and recrystallization of ice. These properties of AFPs have been used to preserve biological samples at a low temperature. Anti-freeze protein (AFP) present in the natural world has a secondary structure of α-helix or β-sheet. Herein, it is know that amino acids T, S and V that can be hydrogen-bonded or hydrophobic interacted with water molecules are arranged at a position in contact with an ice crystal surface in the secondary structure. This arrangement prevents or reduces ice growth or ice recrystallization by interacting with water molecules present on the ice crystal surface at a predetermined interval, thereby inhibiting interaction between the water molecules outside the ice crystal surface (liquid phase) and the molecules on the ice crystal surface. Based on such a technical background, the present inventor prepared a peptide-like structure using a compound capable of having an arrangement similar to a peptide through self-assembly, and confirmed that such a structure has freezing control abilities, and therefore, the present invention has been completed on the basis of the finding.

A composition for controlling freezing according to the present invention includes a compound in which 2 to 5 amino acids, for example, 2, 3, 4, or 5 amino acids are connected to fluorenylmethyloxycarbony (Fmoc) through peptide bonding. The above compound is also referred to as a "peptide-like compound," "sample according to the invention," "sample of the invention," "compound according to the invention," "compound of the invention" or "samples." In addition, the structure formed by self-assembly of the compound is referred to as a "self-assembled nanostructure."

In one embodiment of the present invention, amino acid residues included in the compound may be an amino acid residue selected from the group consisting of arginine (Arg, R), histidine (His, H), lysine (Lys, K), aspartic acid (Asp, D), glutamic acid (Glu, E), serine (Ser, S), threonine (Thr, T), asparagine (Asn, N), glutamine (Gln, Q), cysteine (Cys, C), glycine (Gly, G), proline (Pro, P), alanine (Ala, A), valine (Val, V), isoleucine (Ile, I), leucine (Leu, L), methionine (Met, M), phenylalanine (Phe, F), tyrosine (Tyr, Y), and tryptophan (Trp, W). In another embodiment of the invention, the amino acid may include one or more amino acid residues selected from the group consisting of Thr, Ala, Val, Ser, Cys, Asp, Glu, Phe, and Trp.

In one embodiment of the present invention, the compounds according to the present invention have a structure represented by Fmoc-FFX$_1$, Fmoc-WFX$_1$, Fmoc-WWX$_1$, FmocFWX$_1$, Fmoc-FX$_2$FX$_3$X$_1$, Fmoc-WX$_2$FX$_3$X$_1$, Fmoc-WX$_2$WX$_3$X$_1$, and FmocFX$_2$WX$_3$X$_1$, wherein X$_1$ is any one selected from the group consisting of amino acids T, V, A, S and C, and X$_2$ and X$_3$ are each independently amino acid D or E.

In the compounds according to the present invention, Fmoc and Phe-Phe in the Fmoc-FF induce intermolecular pi-pi stacking and hydrogen bonding, respectively, and are self-assembled to form α-helix or β-sheet, which is similar to the protein secondary structure. Through this arrangement, amino acid residues capable of interacting with water may be arranged outside of the self-assembly to form hydrophilic interaction or hydrophobic interaction, or hydrogen bonding with the ice interface. In addition, it was confirmed that at least one Phe in the Fmoc-FF may be substituted with Trp, and the substituted compound Fmoc-FWX, Fmoc-WFX, or Fmoc-WWX has the same or similar degree of freezing control activities compared to a parent compound Fmoc-FFX.

In one embodiment of the present invention, the $X_1$ is an amino acid capable of interacting with water, in particular, Thr, Ala, Val, Ser, or Cys, and in another embodiment of the present invention, the $X_1$ is Thr, or Ala. The inventor of the present invention has confirmed that when $X_1$ is Thr, Ala, Val, or Ser, it is possible to inhibit recrystallization of ice or to control freezing in all cases, and surprisingly, it was confirmed that, when $X_1$ is Thr having both hydrophobic and hydrophilic functional groups, better ice recrystallization inhibitory activity and/or freezing control activity were/was exhibited than the case of Ser which is an amino acid residue capable of forming a hydrophilic interaction with water or hydrogen bonding, and it was also confirmed that, when $X_1$ is Ala having only the hydrophobic functional group, better ice recrystallization inhibitory activity and/or freezing control activity were/was exhibited than the case of Ser.

In addition, $X_2$ and $X_3$ are each introduced to increase water solubility of the self-assembled nanostructure by increasing a hydrophilicity level of the compound. In one embodiment of the present invention, $X_2$ and $X_3$ are each independently Asp, or Glu, and in another embodiment of the present invention, $X_2$ and $X_3$ are each independently Glu.

In the present disclosure, the compounds according to the invention are named as listed in Table 1 below.

TABLE 1

| Compound | Name |
|---|---|
|  | Fmoc- |
|  | Fmoc-FF |
|  | Fmoc-FFA |
|  | Fmoc-FFS |

TABLE 1-continued
| Compound | Name |
|---|---|
| 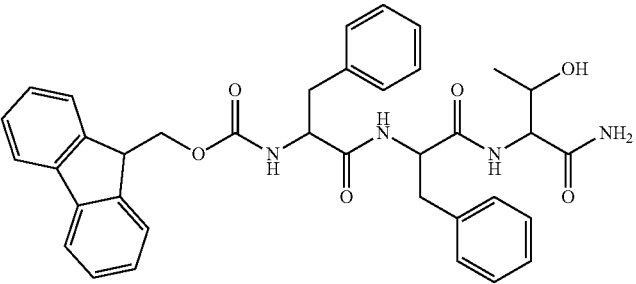 [SMILES: CC(O)C(NC(=O)C(Cc1ccccc1)NC(=O)C(Cc1ccccc1)NC(=O)OCC1c2ccccc2-c2ccccc21)C(N)=O] | Fmoc-FFT |
| 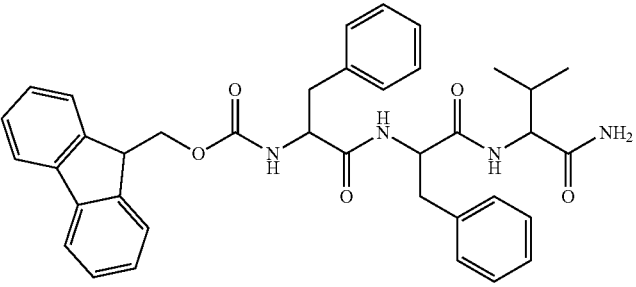 [SMILES: CC(C)C(NC(=O)C(Cc1ccccc1)NC(=O)C(Cc1ccccc1)NC(=O)OCC1c2ccccc2-c2ccccc21)C(N)=O] | Fmoc-FFV |
| 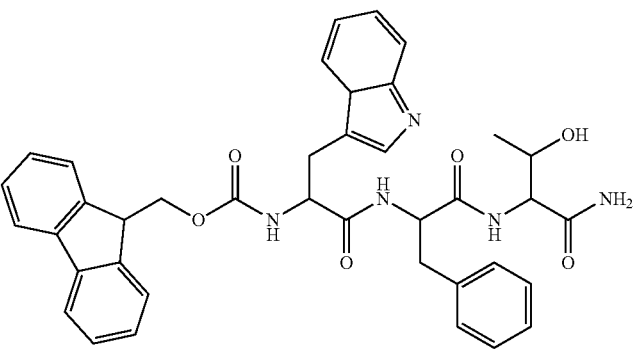 [SMILES: CC(O)C(NC(=O)C(Cc1ccccc1)NC(=O)C(CC1=CN=C2C=CC=CC12)NC(=O)OCC1c2ccccc2-c2ccccc21)C(N)=O] | Fmoc-WFT |
| 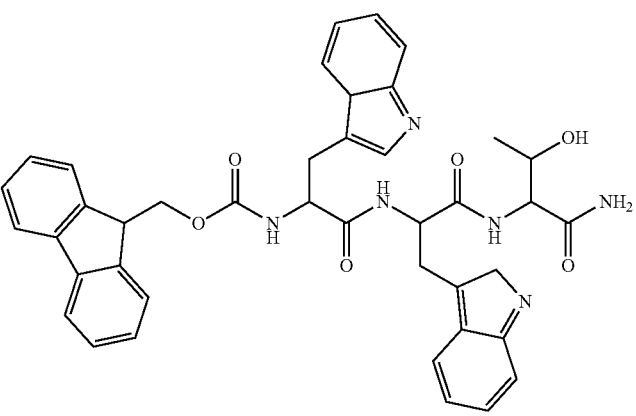 [SMILES: CC(O)C(NC(=O)C(CC1=c2ccccc2=NC1)NC(=O)C(CC1=CN=C2C=CC=CC12)NC(=O)OCC1c2ccccc2-c2ccccc21)C(N)=O] | Fmoc-WWT |

TABLE 1-continued

| Compound | Name |
|---|---|
| (structure) | Fmoc-FEFET |
| (structure) | Naph-FFT |

In one embodiment of the present invention, in order to mimic a high conjugating force between a pyramidal plane and wfAFP, the Thr was intended to be arranged at an interval of about 17.5 Å so that the self-assembled structure of the present invention may effectively conjugated with the crystal plane (Knight, C. A., Cheng, C. C., & DeVries, A. L. (1991). Adsorption of alpha-helical antifreeze peptides on specific ice crystal surface planes. Biophysical Journal, 59(2), 409-418.; Knight, C. A., Driggers, E., & DeVries, A. L. (1993). Adsorption to ice of fish antifreeze glycopeptides 7 and 8. Biophysical Journal, 64(1), 252-259.). In addition, the ice crystal-conjugating surface involved in the AFP characteristics is a basal plane [0001], a primary prism plane [1010], a secondary prism plane [1120], and a pyramidal plane [2021]. Among them, prismatic faces exhibit faster crystal growth than the base plane which exhibits slow crystal growth, and in the case of the pyramidal plane, it is known to be exposed during the ice crystal growth (Lee, H. (2018). Structures, dynamics, and hydrogen-bond interactions of antifreeze proteins in TIP4P/Ice water and their dependence on force fields. PLOS ONE, 13(6), e0198887.; Olijve, L. L. C., Meister, K., DeVries, A. L., Duman, J. G., Guo, S., Bakker, H. J., & Voets, I. K. (2016). Blocking rapid ice crystal growth through nonbasal plane adsorption of antifreeze proteins. Proceedings of the National Academy of Sciences, 113(14), 3740-3745.). Further, it is known that, in the case of wfAFP1 derived from a winter flounder, when conjugated to the pyramidal plane, it has a lower stabilization energy than the basal plane, and in fact, has an interval of 16.5 Å between Thrs regularly present on the surface of wfAFP1, which is coincide with an oxygen-oxygen interval of a pyramidal plane [2021], thus to have a great influence in the process of inhibiting the ice crystal growth. Thereby, Fmoc-FF and Fmoc-FFT were mixed in a molar ratio of 2:1 to be self-assembled in an arrangement of [(Fmoc-FF)(Fmoc-FF)(Fmoc-FFT)], and a composition including such a self-assembly exhibited an equivalent or superior freezing control activity and/or recrystallization inhibitory activity compared to a self-assembled structure composed of one compound.

According to one embodiment of the present invention, there is provided a composition for controlling freezing including a compound represented by Formula 1 or Formula 2 below:

[Formula 1]

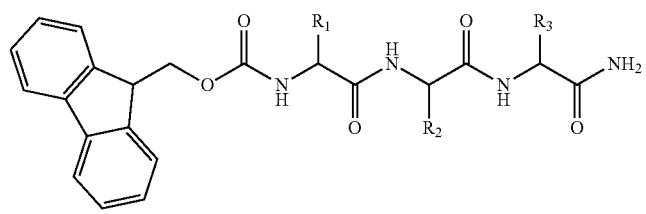

[Formula 2]

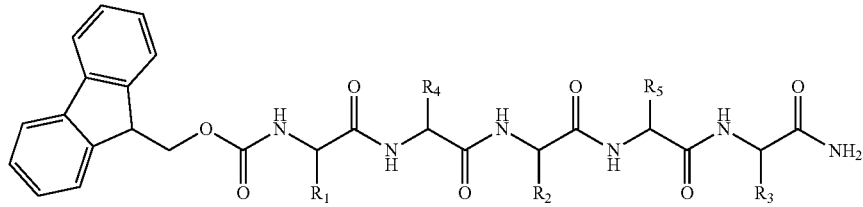

In Formula 1 or 2 above, $R_1$ and $R_2$ are each independently

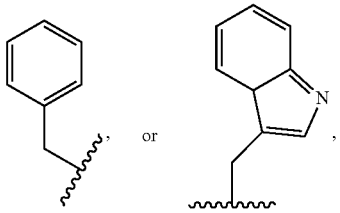 [SMILES: *Cc1ccccc1 ; *CC1=CN=C2C=CC=CC12]

$R_3$ is

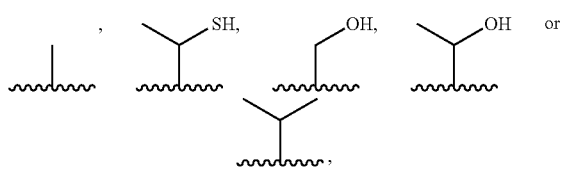

and $R_4$ and $R_5$ are each independently

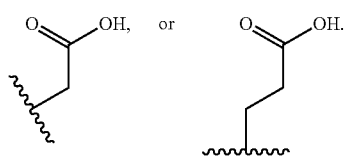 [SMILES: *CC(=O)O ; *CCC(=O)O]

As used herein, the term "ice recrystallization" refers to a process of growing from small ice crystals to larger ice crystals, and the term "Ostwald ripening" refers to such a recrystallization that occurs due to a pressure differential occurring in relation to a difference in energy of the surrounding environment and the surface energy of crystals, which may be performed in a dissolution-diffusion-refreezing or a sublimation-diffusion-condensation mechanism.

As used herein, the terms "antifreezing," "anti-freezing," "freezing control," "freeze control," "freezing inhibition" and "freeze inhibition" are used interchangeably, and refer to actions of lowering a freezing point, preventing ice formation or lowering a speed of ice formation, preventing ice recrystallization, lowering a speed of ice recrystallization, or maintaining a size of ice crystals to be small.

The composition for controlling freezing of the present invention may further include a material having freezing control abilities conventionally known in the art. For example, in one embodiment of the present invention, the composition for controlling freezing may further include, in addition to the self-assembled nanostructure according to the present invention, dimethyl sulfoxide (DMSO), glycerol, 1,2-propanediol, sucrose, glucose, proline, galactose, lactose, glycine betaine, or fructose. In one embodiment of the present invention, when using for cell cryopreservation or food cryopreservation, the composition may further include sucrose, glucose, lactose, glycine betaine, or fructose.

According to one embodiment of the present invention, there is provided a composition for freezing a cell including a compound represented by Formula 1 or Formula 2 above. In the process of freezing and thawing the cells, ice recrystallization may occur. When ice recrystallization occurs, as the ice crystals grow, the cell membrane is damaged and cell dehydration is performed, such that the cells and tissues may be damaged. The composition including the self-assembled nanostructure according to the present invention may inhibit ice growth or recrystallization, thereby preventing apoptosis due to ice crystal growth during cell cryopreservation.

The composition according to the present invention has excellent ice crystal growth inhibitory effect, as well as has low cytotoxicity, and thereby may be usefully used for cryopreservation of cells, tissues, or organs. The cells may be, for example, prokaryotic cells containing microorganisms, plants, animals, fungi, eukaryotic cells including protozoa, for example, sperms, eggs, epithelial cells, nerves cells, epidermal cells, keratinocytes, hematopoietic cells, melanocytes, chondrocytes, B cells, T cells, red blood cells, macrophages, monocytes, fibroblasts, muscle cells, embryonic stem cells, mesenchymal stem cells, or adult stem cells, but it is not limited thereto. In one embodiment of the present invention, the tissue may be an epithelial tissue including membrane epithelial tissue and glandular epithelial tissue; connective tissue including loos connective tissue, adipose tissue, dense fibrous connective tissue, reticular connective tissue, cartilage, bone tissue, blood, and lymph; nerve tissue, including neurons and glials; and muscle tissue including smooth muscle, myocardium, and skeletal muscle, but it is not limited thereto. In one embodiment of the invention, the organs include thyroid, blood vessel, lung, esophagus, liver, spleen, kidney, small intestine, large intestine, organ, heart, urinary tract, and uterus, but it is not limited thereto.

A method for cryopreserving the cells, tissues, or organs includes contacting or adding an effective amount of a self-assembled nanostructure according to the present invention to a subject to be cryopreserved, and cooling to a temperature for cryopreservation. The method of cryopreserving the cells, tissues, or organs may be performed by using techniques known in the art, for example, may use a rapid cooler, or liquid nitrogen, but it is not limited thereto.

In one embodiment of the present invention, the composition according to the present invention may be used to cryopreserve germ cells including sperms and eggs, and stem cells. Cryopreservation of germ cells is widely studied in biotechnology for assisted reproductive technologies (ARTs) and as an important technique for breeding management in the case of livestock. Meanwhile, after thawing, sperm quality is deteriorated to cause a deterioration in fertility. As main causes thereof, rapid temperature changes, ice formation, and osmotic pressure are suggested. It was confirmed that, when using the self-assembled nanostructures having biocompatibility according to the present invention, ice formation and/or recrystallization were/was inhibited, thereby minimizing osmotic pressure changes due to an increase in the local concentration within a cell, solvent, or medium, and consequently, the survival rate and fertility of sperm thawed after freezing could be increased.

According to one embodiment of the present invention, there is provided a composition for food cryopreservation including a compound represented by Formula 1 or Formula 2 above. In the process of freezing and/or thawing the food, ice crystals generated from moisture grow, which destroys the cells and/or tissue present in the food, thereby causing a reduction in a texture of food. Since the self-assembled nanostructure according to the present invention inhibits freezing and/or inhibits recrystallization of ice, it is possible to minimize a degradation in food quality due to ice crystal growth and the osmotic pressure change.

The method of cryopreserving a food includes contacting or adding an effective amount of the self-assembled nanostructure according to the present invention to an object to be cryopreserved, and cooling to a temperature for cryopreservation. The cryopreservation method may be performed using techniques known in the art, and for example, may use a rapid cooler or liquid nitrogen, but it is not limited thereto.

Those skilled in the art will understand the case in which "about" should be used unavoidably, and the term "about" as used herein will be understood to include numerical values within a margin of error.

The term "substantially the same" as used herein means a case in which there is a difference in the same or unrecognized degree within the margin of error. As used herein, the term "substantially free," "be substantially free" or similar expressions thereto refer to a case of zero or zero is included within the margin of error, or a case of negligible for those skilled in the art to recognize.

EXAMPLE

Preparative Example 1. Preparation of Fmoc-FF

Fmoc-FF was synthesized on a Rink Amide MBHA resin using a standard solid-phase peptide synthesis (SPPS) method in a CEM Focused Microwave™ Synthesis System, Discover. After washing the resin with dichloromethane (DCM), the resin was expanded in a solution in which dimethylformamide (DMF) and DCM are mixed in a ratio of 1:1 in an incubator equipped with a stirrer for 30 minutes. Fmoc portion of the resin was removed in microwave for 3 minutes with 20% piperidine in DMF and washed thoroughly with DMF, DCM and N-Methyl-2-pyrrolidone (NMP). Then, an NMP solution, in which Fmoc-Phe-OH (5.0 equivalents), O-(Benzotriazol-1-yl)-N,N,N',N'-tetramethyluronium hexafluorophosphate (HBTU) (4.9 equivalents) and N,N-Diisopropylethylamine (DIPEA) (5.0 equivalents) are mixed, was added to the resin and treated in the microwave for 10 minutes. Thereafter, Fmoc-Phe-OH was coupled with an N-terminal of peptide on the resin in an order of Fmoc-FF-resin. The presence of a free amino group was confirmed through Kaiser test for each of coupling and protecting group removal processes. The resin was treated with a cleavage solution (trifluoroacetic acid (TFA):triisopropylsilane (TIS):$H_2O$=95:2.5:2.5) in the incubator equipped with a stirrer for 2 hours. Excess TFA was removed with argon gas, and the product was precipitated in cold $Et_2O$, and then centrifuged at 4000 rpm for 5 minutes. Peptides were purified using a linear gradient of water (0.1% TFA) and acetonitrile (0.1% TFA) at a rate of 2 mL min$^{-1}$ in a C18 column (SUPELCO, Discovery® BIO Wide Pore C18, 5 µm, 10×250 mm) by reverse phase HPLC. Then, the peptides were confirmed by UV absorption spectra at 230 nm and 254 nm. A molecular weight of Fmoc-FF (557 [M+Na]$^+$) was confirmed by a MALDI-TOF/TOF mass spectrometer.

Preparative Example 2. Preparation of Fmoc-FFX

Fmoc-FFX was synthesized on a Rink Amide MBHA resin using a standard solid phase peptide synthesis method in a CEM Focused Microwave™ Synthesis System, Discover. After washing the resin with DCM, the resin was expanded in a solution in which DMF and DCM are mixed in a ratio of 1:1 in an incubator equipped with a stirrer for 30 minutes. Fmoc portion of the resin was removed in microwave for 3 minutes with 20% piperidine in DMF and washed thoroughly with DMF, DCM and NMP. Then, an NMP solution, in which Fmoc-Thr(tBu)-OH (5.0 equivalents) for Fmoc-FFT, Fmoc-Val-OH (5.0 equivalents) for Fmoc-FFV, Fmoc-Ala-OH (5.0 equivalents) for Fmoc-FFA, and Fmoc-Ser(tBu)-OH (5.0 equivalents) for Fmoc-FFS; HBTU (4.9 equivalents) and DIPEA (5.0 equivalents) are mixed respectively, was added to the resin and treated in the microwave for 10 minutes. Thereafter, Fmoc-Phe-OH was coupled with an N-terminal of peptide on the resin in an order of Fmoc-FF-resin. The presence of a free amino group was confirmed through Kaiser test for each of coupling and protecting group removal processes. The resin was treated with a cleavage solution (TFA:TIS:$H_2O$=95:2.5:2.5) in the incubator equipped with a stirrer for 2 hours. Excess TFA was removed with argon gas, and the product was precipitated in cold $Et_2O$, and then centrifuged at 4000 rpm for 5 minutes. Peptides were purified using a linear gradient of water (0.1% TFA) and acetonitrile (0.1% TFA) at a rate of 2 mL min$^{-1}$ in a C18 column (SUPELCO, Discovery® BIO Wide Pore C18, 5 µm, 10×250 mm) by reverse phase HPLC. Then, the peptides were confirmed by UV absorption spectra at 230 nm and 254 nm. A molecular weight of Fmoc-FFT (657 [M+Na]$^+$), a molecular weight of Fmoc-FFV (655 [M+Na]$^+$, 671 [M+K]$^+$), a molecular weight of Fmoc-FFA (627 [M+Na]$^+$), and molecular weights of Fmoc-FFS (643 [M+Na]$^+$, 659 [M+K]$^+$) were confirmed by a MALDI-TOF/TOF mass spectrometer.

Preparative Example 3. Preparation of Fmoc-FEFET

Fmoc-FEFET was synthesized on a Rink Amide MBHA resin using a standard solid phase peptide synthesis method in a CEM Focused Microwave™ Synthesis System, Discover. After washing the resin with DCM, the resin was expanded in a solution in which DMF and DCM are mixed in a ratio of 1:1 in an incubator equipped with a stirrer for 30 minutes. Fmoc portion of the resin was removed in microwave for 3 minutes with 20% piperidine in DMF and washed thoroughly with DMF, DCM and NMP. Then, an NMP solution, in which Fmoc-Thr(tBu)-OH (5.0 equivalents); HBTU (4.9 equivalents); and DIPEA (5.0 equivalents) are mixed respectively, was added to the resin and treated in the microwave for 10 minutes. Thereafter, Fmoc-Glu(OtBu)-OH and Fmoc-Phe-OH were coupled with an N-terminal of peptide on the resin in an order of Fmoc-FEFET-resin. The presence of a free amino group was confirmed through Kaiser test for each of coupling and protecting group removal processes. The resin was treated with a cleavage solution (TFA:TIS:H$_2$O=95:2.5:2.5) in the incubator equipped with a stirrer for 2 hours. Excess TFA was removed with argon gas, and the product was precipitated in cold Et$_2$O, and then centrifuged at 4000 rpm for 5 minutes. Peptides were purified using a linear gradient of water (0.1% TFA) and acetonitrile (0.1% TFA) at a rate of 2 mL min$^{-1}$ in a C18 column (SUPELCO, Discovery® BIO Wide Pore C18, 5 μm, 10×250 mm) by reverse phase HPLC. Then, the peptides were confirmed by UV absorption spectra at 230 nm and 254 nm. Molecular weights of Fmoc-FEFET (915 [M+Na]$^+$, 932 [M+K]$^+$) were confirmed by a MALDI-TOF/TOF mass spectrometer.

Preparative Example 4. Preparation of Fmoc-WFT

Fmoc-WFT was synthesized on a Rink Amide MBHA resin using a standard solid phase peptide synthesis method in a CEM Focused Microwave™ Synthesis System, Discover. After washing the resin with DCM, the resin was expanded in a solution in which DMF and DCM are mixed in a ratio of 1:1 in an incubator equipped with a stirrer for 30 minutes. Fmoc portion of the resin was removed in microwave for 3 minutes with 20% piperidine in DMF and washed thoroughly with DMF, DCM and NMP. Then, an NMP solution, in which Fmoc-Thr(tBu)-OH (5.0 equivalents); HBTU (4.9 equivalents); and DIPEA (5.0 equivalents) are mixed respectively, was added to the resin and treated in the microwave for 10 minutes. Thereafter, Fmoc-Trp-OH and Fmoc-Phe-OH were coupled with an N-terminal of peptide on the resin in an order of Fmoc-WFT-resin. The presence of a free amino group was confirmed through Kaiser test for each of coupling and protecting group removal processes. The resin was treated with a cleavage solution (TFA:TIS:H$_2$O=95:2.5:2.5) in the incubator equipped with a stirrer for 2 hours. Excess TFA was removed with argon gas, and the product was precipitated in cold Et$_2$O, and then centrifuged at 4000 rpm for 5 minutes. Peptides were purified using a linear gradient of water (0.1% TFA) and acetonitrile (0.1% TFA) at a rate of 2 mL min$^{-1}$ in a C18 column (SUPELCO, Discovery® BIO Wide Pore C18, 5 μm, 10×250 mm) by reverse phase HPLC. Then, the peptides were confirmed by UV absorption spectra at 230 nm and 254 nm. Molecular weights of Fmoc-WFT (674 [M+H]$^+$, 696 [M+Na]$^+$) were confirmed by a MALDI-TOF/TOF mass spectrometer.

Preparative Example 5. Preparation of Fmoc-WWT

Fmoc-WWT was synthesized on a Rink Amide MBHA resin using a standard solid-phase peptide synthesis method in a CEM Focused Microwave™ Synthesis System, Discover. After washing the resin with DCM, the resin was expanded in a solution in which DMF and DCM are mixed in a ratio of 1:1 in an incubator equipped with a stirrer for 30 minutes. Fmoc portion of the resin was removed in microwave for 3 minutes with 20% piperidine in DMF and washed thoroughly with DMF, DCM and NMP. Then, an NMP solution, in which Fmoc-Thr(tBu)-OH (5.0 equivalents); HBTU (4.9 equivalents); and DIPEA (5.0 equivalents) are mixed respectively, was added to the resin and treated in the microwave for 10 minutes. Thereafter, Fmoc-Trp-OH was coupled with an N-terminal of peptide on the resin in an order of Fmoc-WWT-resin. The presence of a free amino group was confirmed through Kaiser test for each of coupling and protecting group removal processes. The resin was treated with a cleavage solution (TFA:TIS:H$_2$O=95:2.5:2.5) in the incubator equipped with a stirrer for 2 hours. Excess TFA was removed with argon gas, and the product was precipitated in cold Et$_2$O, and then centrifuged at 4000 rpm for 5 minutes. Peptides were purified using a linear gradient of water (0.1% TFA) and acetonitrile (0.1% TFA) at a rate of 2 mL min$^{-1}$ in a C18 column (SUPELCO, Discovery® BIO Wide Pore C18, 5 μm, 10×250 mm) by reverse phase HPLC. Then, the peptides were confirmed by UV absorption spectra at 230 nm and 254 nm. Molecular weights of Fmoc-WWT (714 [M+H]$^+$, 736 [M+Na]$^+$, 752 [M+K]$^+$) were confirmed by a MALDI-TOF/TOF mass spectrometer.

Preparative Example 6. Preparation of Naph-FFT

Naph-FFT was synthesized on the Rink Amide MBHA resin using a standard solid phase peptide synthesis method from the CEM Focused Microwave™ Synthesis System, Discover. After washing the resin with DCM, the resin was expanded in a solution in which DMF and DCM are mixed in a ratio of 1:1 in an incubator equipped with a stirrer for 30 minutes. Fmoc portion of the resin was removed in microwave for 3 minutes with 20% piperidine in DMF and washed thoroughly with DMF, DCM and NMP. Then, an NMP solution, in which Fmoc-Thr(tBu)-OH (5.0 equivalents); HBTU (4.9 equivalents); and DIPEA (5.0 equivalents) are mixed respectively, was added to the resin and treated in the microwave for 10 minutes. Thereafter, Fmoc-Phe-OH was coupled with an N-terminal of peptide on the resin in an order of Naph-FFT-resin. Fmoc was substituted with 1-naphthylacetic acid through the same coupling process. The presence of a free amino group was confirmed through Kaiser test for each of coupling and protecting group removal processes. The resin was treated with a cleavage solution (TFA:TIS:H$_2$O=95:2.5:2.5) in the incubator equipped with a stirrer for 2 hours. Excess TFA was removed with argon gas, and the product was precipitated in cold Et$_2$O, and then centrifuged at 4000 rpm for 5 minutes. Peptides were purified using a linear gradient of water (0.1% TFA) and acetonitrile (0.1% TFA) at a rate of 2 mL min$^{-1}$ in a C18 column (SUPELCO, Discovery® BIO Wide Pore C18, 5 μm, 10×250 mm) by reverse phase HPLC. Then, the peptides were confirmed by UV absorption spectra at 230 nm and 254 nm. Molecular weight of Naph-FFT (603 [M+Na]$^+$, 619 [M+K]$^+$) were confirmed by a MALDI-TOF/TOF mass spectrometer.

It was confirmed that Fmoc-FF, Fmoc-FFT, Fmoc-FFV, Fmoc-FFA, Fmoc-FFS, Fmoc-FEFET, Fmoc-WFT, Fmoc-WWT, and Naph-FFT were successfully prepared according to Preparative Examples 1 to 6 above through HPLC (FIG. 1), and MALDI/TOF-TOF (FIG. 2).

Preparative Example 7. Formation of Nanostructure

Self-assembled nanostructures were prepared by adding all the compounds synthesized in Preparative Examples 1 to 6 above to deionized water at a concentration of 10 to 20 μM in consideration of the critical concentration.

7.1 Fmoc-FF

It could be confirmed that the synthesized Fmoc-FF exhibited positive maximum ellipticity at 195 nm and negative minimum ellipticity at 220 nm upon CD spectroscopy experiment, and thus it had a typical beta sheet secondary structure in an aqueous solution. In addition, it could be seen that the synthesized Fmoc-FF had a critical micellar concentration (CMC) of 17 µM through a difference in emission intensity depending on the concentration. Further, it was confirmed that the Fmoc-FF forms fibrils having a thickness of 5 nm in an aqueous solution through a transmission electron microscopy (TEM) experiment (FIG. 3).

7.2 Fmoc-FFT, Fmoc-FFV, Fmoc-FFA, and Fmoc-FFS

It was confirmed that all the synthesized Fmoc-FF-based Fmoc-FFT, Fmoc-FFV, Fmoc-FFA, and Fmoc-FFS peptides had a beta sheet secondary structure through CD spectroscopy (FIG. 4). However, shapes of the self-assembled nanostructure were different from each other depending on the compound (FIG. 5). It was confirmed that Fmoc-FFT in which Thr residue was introduced into Fmoc-FF maintains a 1D fibril structure, whereas in the case of Fmoc-FFV in which a hydroxyl group of Thr residue in the Fmoc-FFT is substituted with a methyl group, hydrophobic interaction was strengthened to form a 2D sheet, and also in the case of Fmoc-FFA which does not include both a methyl group and a hydroxyl group, a 2D sheet structure or a ribbon structure was formed, and in the case of Fmoc-FFS from which the methyl group is removed, the fibrils were maintained as they are.

7.3 Fmoc-FEFET

It could be confirmed that Fmoc-FEFET had CMC increased to 22.8 µm compared to Fmoc-FFT, and solubility was improved. In addition, it was confirmed that the Fmoc-FEFET had a beta-sheet secondary structure and forms fibrils which are very well dispersed in an aqueous solution by cryo-TEM and TEM (FIG. 6).

7.4 Co-assembly of Fmoc-FF and Fmoc-FFT

Fmoc-FF and Fmoc-FFT were mixed in a ratio of 2:1 (mole:mole) to prepare a co-assembly of FmocFF: FmocFFT. It was confirmed that Fmoc-FF and Fmoc-FFT were similar to each other in terms of CMC, and the co-assembly had uniform dispersibility through DLS spectroscopy and the shapes of the nanostructures maintained the fibrils as they are through a TEM experiment (FIG. 7).

7.5 Fmoc-WFT, Fmoc-WWT, and Naph-FFT

It was confirmed that, in the case of Fmoc-WFT and Fmoc-WWT, random coils and alpha-helix secondary structures were predominantly formed. In particular, it was confirmed that, in the case of Fmoc-WWT in which all F were replaced with W, helical fibrils were formed (FIG. 8).

Example 1. Effect of Freezing Control

Example 1.1 Analysis of Anti-Freezing Effect Using Color Change of Gold Nanoparticles (TH, Evaluation of IRI)

Thermal hysteresis (TH) as anti-freezing activity was measured in accordance with the method described in Park, J.-I., Lee, J. H., Gwak, Y., Kim, H. J., Jin, E., & Kim, Y.-P. (2013). Frozen assembly of gold nanoparticles for rapid analysis of antifreeze protein activity. *Biosensors and Bioelectronics*, 41, 752-757, and ice recrystallization inhibition (IRI) activity was measured based on Mitchell, D. E., Congdon, T., Rodger, A., & Gibson, M. I. (2015). Gold Nanoparticle Aggregation as a Probe of Antifreeze (Glyco) Protein-Inspired Ice Recrystallization Inhibition and Identification of New IRI Active Macromolecules. *Scientific Reports*, 5(1). More specifically, when dispersing AFP in a solution in which gold nanoparticles are dispersed, and freezing the solution then thawing again, if the AFP has good conjugating force with an ice crystal surface, the dispersibility of gold nanoparticles is good to maintain an original color of the solution, whereas if it has weak conjugating force, AFP is precipitated, and when ice crystals are rapidly formed, the solution is subjected to color change.

Example 1.1.1 Synthesis of Gold Nanoparticles

Gold nanoparticles (Cit-AuNP) stabilized with citric acid were synthesized to prepare mercaptopropionic acid (MPA)-AuNP. 20 mL of a storage solution containing 1 mM $HAuCl_4 \cdot 3H_2O$ was added to 50 mL of deionized water (DI water). After the solution was stirred and heated to a boiling point, 30 mM sodium citric acid in 2 mL of deionized water was further added to the solution and heated for 20 minutes. The color of the solution changed from bright yellow to burgundy. Thereafter, the solution was cooled to room temperature while stirring and further stirred for 1 hour. An average size of MPA-capped AuNP was measured to be about 16.7 nm.

Example 1.1.2 Colorimetric Assay

On a microwell plate, 50 µL of a solution containing 0.5 mM sample was added to 350 µL of 300 µM MPA-AuNP solution, respectively. As a control, 350 µL of 300 µM MPA-AuNP solution was used. The microwell plate containing the sample mixture was cooled to −65° C. for 23 minutes, and the temperature was increased at room temperature until completely dissolved. During the freezing process, the sample was observed every 5 minutes, and after 20 minutes therefrom, the sample was confirmed every 1 minute. To quantitatively confirm the color change before and after freezing, absorption spectra of each mixture were measured with a UH5300 spectrometer before and after freezing. The spectra were measured from 300 nm to 900 nm at a scan speed of 400 nm/min, and aggregation properties (E525/E650) of each mixture were compared.

Example 1.1.3 Measurement of TH and IRI Activities of BSA and PEG

Bovine serum albumin (BSA) which is known to have an effect of inhibiting ice recrystallization, and polyethylene glycol (PEG) which has no effect of inhibiting ice recrystallization were used to confirm reliability of the above experiment. When adding BSA, there was no color change since aggregation did not occur, but the color change occurred in the PEG-added solution, and it was confirmed that aggregation occurred therethrough (FIG. 9). Through this experiment, it was proved that floating effect could be checked.

Example 1.1.4 Measurement of TH and IRI Activities of Fmoc-FF, Fmoc-FFX, Fmoc-FEFET, Fmoc-FF:FmocFFT=2:1, Fmoc-WFT, Fmoc-WWT and Naph-FFT It could be confirmed that, when specifically adding gold particles showing the strongest absorption at 525 nm with Fmoc-WFT and Fmoc-WWT after freezing/thawing of the solution, an aggregation phenomenon was exhibited, such that the absorption peak was partially shifted to 650 nm (FIG. 10). This can be described by the fact that, in the case of the two samples, the regular arrangement of the threonine (Thr) on the surface, i.e., the residues conjugated to the ice varies, because the secondary structure deviates from the beta-sheet shape, unlike other samples.

Example 1.2 Analysis of IRI Activity Using Splat Assay

In order to more clearly confirm the effect of inhibiting ice crystal growth, ice recrystallization inhibition (IRI) characteristics were analyzed. Analysis of ice recrystallization was performed by reference Mitchell, D. E., Clarkson, G., Fox, D. J., Vipond, R. A., Scott, P., & Gibson, M. I. (2017). Antifreeze Protein Mimetic Metallohelices with Potent Ice Recrystallization Inhibition Activity. *Journal of the American Chemical Society*, 139(29), 9835-9838 and Budke, C., Heggemann, C., Koch, M., Sewald, N., & Koop, T. (2009). Ice Recrystallization Kinetics in the Presence of Synthetic Antifreeze Glycoprotein Analogues Using the Framework of LSW Theory. *The Journal of Physical Chemistry B*, 113(9), 2865-2873. More specifically, a 10 μL sample was dropped from a height of 1.5 m onto a surface of a cover glass precooled to −60° C. so as to form a thin film of ice. The cover glass with the thin ice film formed thereon was transferred to a Peltier cooler set at −20° C., and the surface of the cover glass was gradually increased to −6° C. at a rate of 5 $min^{-1}$, and the sample was annealed for 30 minutes. During recrystallization of ice, dark-field optical microscopy (DFOM) images were taken, and ten of the largest ice crystal domains were chosen and a mean value thereof was obtained to evaluate the IRI activity. A mean largest grain size (MLGS) analysis was repeated three times.

It was confirmed that the Fmoc-FFT, Fmoc-FFV, Fmoc-FFA, and Fmoc-FFS had the IRI effect, and the IRI effect was determined by quantitative analyzing DFOM images (FIG. 12a) obtained during ice recrystallization when thawing after freezing. The Fmoc-FFT exhibited the highest IRI activity, followed by the Fmoc-FFA, FFV and FFS had higher IRI activity in this order. Through this, it was confirmed that the presence of both hydrophilic and hydrophobic residues is important in the freezing inhibitory activity. That is, it is considered that ice growth can be inhibited by a method in which the hydrophilic groups form hydrogen bonding with water and the hydrophobic groups trap water therebetween.

In the case of Fmoc-FEFET nanofibrils, it was confirmed that they have a similar to or slightly higher IRI effect than the Fmoc-FFT, and it was confirmed that, in the case of the nanofibrils in which Fmoc-FF and Fmoc-FFT inducing conjugating with a pyramidal plane are co-assembled, they had a slightly higher IRI effect (FIG. 13).

In addition, it was shown that, in the case of Naph-FFT in which Fmoc of Fmoc-FFT was substituted with naphthalene, and Fmoc-WFT and Fmoc-WWT in which at least one phenylalanine was replaced with tryptophan, that is, hydrophobic amino acid, all of them had IRI effects (FIG. 14).

Example 2. Evaluation of Toxicity and Cryopreservation Effect on Stem Cell and Germ Cell Example 2.1 Cell Experiment Method Example 2.1.1 Animal C57BL/6J mice (OrientBio Korea) were used as sperm donors (12 to 15 weeks old) and egg donors (8 to 10 weeks old). Ten genetically modified mice based on C57BL/6 were used for in vitro fertilization (IVF) and embryo transfer. ICR mice (8 to 10 weeks old, SLC JAPAN) were used as a consumer of 2-cell embryo.

Example 2.1.2 Medium

To cryopreserve sperms, a modified 18% raffinose pentahydrate/3% skim milk (Difco, Becton Dickinson) solution containing 100 mM L-glutamine or skim milk, to which a cryoprotectant according to the present invention was added, was prepared. A human tubal fluid (HTF) medium was used during the IVF process, and a potassium simplex optimized medium (PSOM) was used while 2-cell embryo was cultured to a blastocyst stage.

Example 2.1.3 Sperm Freezing and Thawing

A sperm cryopreservation solution dispensed in 60 μL was placed in a 35 mm culture dish and covered with paraffin oil. After male mice were sacrificed with cervical potential, a tail of epididymis was removed and divided into pieces, and all fats and blood were removed while observing under a microscope before transferring to the cryopreservation solution. The culture dish was kept at 37° C. for 3 minutes and gently stirred every minute to allow sperms to disperse from the tissues. During preparing the sperms, 100 μL of cryopreservation solution and 15 mm air were injected into a freezing straw using a 1 mL syringe. Sperm suspension was injected into the freezing straw and both ends sealed. The sealed freezing straw was transferred to a freezing container and placed in liquid nitrogen for storage. Before an IVF experiment, the sample was taken out of liquid nitrogen and thawed in a 37° C. constant temperature water bath for 10 minutes.

Example 2.1.4 In Vitro Fertilization

Adult female mice were injected with 7.5 IU of horse chorionic gonadotropin intraperitoneally to induce ovulation and, after 48 hours, 7.5 IU of human chorionic gonadotropin (hCG) was injected. After 15 hours, the mice were sacrificed and the oviduct was quickly removed, then transferred to a fertilization dish containing paraffin oil. Thereafter, 4 to 6 egg-cumulus complexes were obtained from the fallopian tube bulge of 2 to 3 female mice, and 90 μL of HTF medium was added to the eggs.

Frozen sperms were thawed under various conditions, then added to IVF drops containing eggs and incubated at 37° C. (final locomotor sperm concentration: 200-400 sperm/μl). After 6 hours, the fertilized eggs were washed three times in HTF drops. After 24 hours from fertilization, a fertilization rate was calculated using the total number of 2-cell embryos as a percentage based on the total number of eggs.

Example 2.1.5 Embryo Culture and Implantation

After performing IFV, 2-cell embryos were classified into a group to be cultured in the blastocyst stage and a group to be implanted in the oviduct of ICR females. After giving birth, the number of pups was recorded.

Example 2.1.6 Statistic Assay

Student's t test was used for comparison between the two groups, and one-way or two-way ANOVAs were used for a plurality of groups. All data are marked by mean±SEM.

Asterisks indicate statistically significant levels (*, P<0.05, and **, P<0.01). P<0.05 was considered statistically significant.

Example 2.1.7 Mouse Embryonic Stem Cell Culture

In a 60 mm cell culture dish coated with 0.1% gelatin (Sigma), mouse ES cells were cultured in a medium DMEM (Hyclone), to which 2 mM L-glutamine (Mediatech Inc.), 1% penicillin/streptomycin (Mediatech Inc.), 15% heat-inactivated fetal bovine serum (Hyclone), 20 mM HEPES-pH 7.3 (Cellgro), 0.1 mM MEM non-essential amino acid (Cellgro), 0.1 mM 2-mercaptoethanol (Sigma) and 1000 U/mL LIF (Millipore) are added, in order to prevent differentiation.

Example 2.1.8 Analysis of Mouse Embryonic Stem Cell Viability

Mouse ES cells were seeded by $8 \times 10^4$ cells per well in a 96-well plate containing the above various cryopreservation solutions. After 9 hours, CCK-8 reagent was added and fluorescence intensity was measured using an ELISA Reader (TECAN).

Example 2.1.9 Mouse Embryonic Stem Cell Freezing and Thawing

250 μL of trypsinized mouse ES cells, 200 μL of FBS and 50 μL of cryopreservation solution (0.005 μM, 0.01 μM, 0.05 μM, and 0.1 μM) were frozen in a rapid freezer for 2 days, and then stored in an LN2 tank. Thawing was performed in a 37° C. constant temperature water bath. The cell frozen stock mixture was inoculated in 4.5 mL medium of 15 mL tube, and then centrifuged at 1000 rpm for 5 minutes. Cell pellets were added with 1 mL medium and inoculated in a 6-well plate.

Example 2.1.10 Crystal Violet Dye

Mouse ES cells were cultured in 2.5 μM to 10 PM cryopreservation solution for 12 hours. Cells were washed with 500 μL of PBS and 500 μL of 4% PFA was added thereto for 15 minutes. The fixed cells were washed twice with 500 μL of PBS and 0.5% crystal violet solution was added thereto for 30 minutes. The stained cells were washed with tap water.

Example 2.2 Toxicity and Cryopreservation Effect on Mouse Embryonic Stem Cells (mESCs)

Cryopreservation effects were confirmed for stem cells of Fmoc-FF, Fmoc-FFT, Fmoc-FFA, Fmoc-FEFET, and Fmoc-FF+Fmoc-FFT (2:1 mole:mole).

Example 2.2.1 Evaluation of Cell Viability of mESC Using CCK-8 Assay

After treating the mESC within a range of 5 to 20 uM for the Fmoc-FF, Fmoc-FFT, Fmoc-FFA, Fmoc-FEFET, and Fmoc-FF+Fmoc-FFT (2:1 mole:mole), cell viability was confirmed using CCK-8 assay with chemical cryoprotectant DMSO as controls.

As can be seen from crystal violet dye images, DMSO exhibited high toxicity to the cells. Meanwhile, Fmoc-FF, Fmoc-FFT, Fmoc-FFA, Fmoc-FEFET, and Fmoc-FF+Fmoc-FFT (2:1 mole:mole) according to the present invention exhibited no toxicity (FIG. 15a to c), through this, it was confirmed that the material according to the present invention is a biocompatible material.

In addition, it was confirmed that Fmoc-FFV, Fmoc-FFS, Fmoc-WFT, Fmoc-WWT, and Naph-FFT also exhibited significant cell viability with respect to mESC (FIG. 16).

Example 2.2.2 Cryopreservation Activity for mESC

A cell storage solution was prepared with a sample solution 10% (v/v), FBS 40% (v/v), and media 50% (v/v) according to the present invention, and frozen at −80° C. using a rapid freezer, then the cells were stored for 2 days, and further stored in a liquid nitrogen tank for 2 days or more. Then, the cells were thawed and used in the experiment. In addition, the cells were cultured by treatment with a leukemia inhibitory factor (LIF) to confirm the differentiation ability of stem cells. All the controls were cultured and differentiated under the same conditions, except that deionized water was added instead of the sample according to the present invention.

When freezing and thawing the cells using Fmoc-FF, Fmoc-FFT, Fmoc-FFA, Fmoc-FEFET, and Fmoc-FF+Fmoc-FFT (2:1 mole:mole) according to the present invention, it was confirmed that survival and proliferation of mESC was smoothly performed, whereas most of the cells were killed in the controls (FIG. 17a). In addition, when confirming the cell differentiation of mESC until 4 days later (FIG. 17b), it was confirmed that the material according to the present invention may be used as a cryoprotectant for stem cells, and it was confirmed that cell differentiation occurs well even at a high concentration (FIG. 18).

Example 2.3 Cryopreservation Effect of Germ Cell Sperm

After freezing and thawing sperms with 3% skim milk; and Fmoc-FF, Fmoc-FFT, Fmoc-FFA, Fmoc-FFS, Fmoc-FFV, Fmoc-WFT, Fmoc-WWT, Naph-FFT, or Fmoc-FF+Fmoc-FFT (2:1 mole:mole) according to the method of Example 2.2.2 above, in vitro fertilization (IVF) was performed on eggs to confirm whether embryonic cells are produced, thereby confirming whether frozen and thawed germ cells maintain germinal function. In addition, it was studied whether the cryopreserved sperms maintain their function through direct fertilized egg transplantation into mice.

First, the sperms were frozen in a co-assembled fiber material, Fmoc-FF+Fmoc-FFT (2:1 mole:mole) and 3% skim milk, and the number of fertilized eggs formed by fertilizing the eggs was counted. Herein, it was confirmed that 70% or more of fertilized eggs in 2.5 to 7.5 μM, and 50% or more of fertilized eggs in 2.5 to 10 μM were formed (FIG. 19).

In addition, the sperms were frozen in 3% skim milk containing 10 to 20 μM with respect to the nine materials according to the present invention, and then injected into oocytes, followed by separation 2-cell embryos in the process of zygote development. Thereafter, it was attempted to confirm the cryopreservation effect by checking the maturation process into blastocysts (FIG. 20). It was confirmed that 2-cell embryo was formed at a rate of 60% or more when fertilizing the thawed sperms in the eggs, and specifically, in the case of Fmoc-WWT, 2-cell embryo was produced with a high efficiency of 77% or more. The rate of blastocyst production in all the isolated 2-cell embryos exhibited 70% or more, especially in the case of co-assembled Fmoc-FF+Fmoc-FFT (2:1 mole:mole) which induce conjugating with a pyramidal plane, it was confirmed that the 2-cell embryo was formed in a ratio of 70% or more, and the blastocyst was formed in 92% or more. It was determined that ice growth is inhibited, and the shape of the generated ice induces a spherical ice growth process rather than a needle shape.

Since the blastocyst has a shape when the fertilized egg implants on a wall of uterus, as a result of injecting sixty 2-cell embryos into the uterus of three female mice (C57BL/6), it was confirmed that 50 to 60% of the born mice survive healthy (FIG. 21).

Example 3. Effect of Freezing Control on Food

In order to determine whether Fmoc-FFT can be used as a cryoprotectant for foods, Fmoc-FFT was added to beef (FIG. 22a), then frozen at −20° C. for one day, thawed at room temperature, and then SEM images were observed (FIGS. 22b and d). When Fmoc-FFT was not added, a tissue surface was very rough and large pores were found (FIG. 22b), whereas when Fmoc-FFT was added, the tissue surface was very smooth and large pores were not found between tissues (FIG. 22d).

After freezing and thawing, Fmoc-FFT was added to water in order to confirm the beef tissue, frozen at −20° C., then the process of recrystallization of ice was observed under an optical microscope. As a result, when Fmoc-FFT was added (FIG. 22e), it was confirmed that the size of recrystallized ice was significantly smaller than the case where the Fmoc-FFT was not added (FIG. 22c).

Further, in order to confirm the tissue change in more detail, the thawed tissue was rapidly frozen in liquid nitrogen, then cut while maintaining −20° C., and the internal tissue was checked. It was confirmed that, when the Fmoc-FFT was added to meat (right in FIG. 22e), the size of the recrystallized ice was remarkably smaller than the case where the Fmoc-FFT was not added (right in FIG. 22c). It was observed that, when the Fmoc-FFT was not added, the size of tissue pore was 22±8.6 μm, while it was 5±2.3 μm when adding the same.

For purpose of understanding technical configurations of the claims, the appended claims described below should not be interpreted narrowly than words applied literally in any way, therefore, illustrative embodiments in the specification could not be directly considered as the claims. Accordingly, it is duly understood that the present invention has been described with reference to illustrative embodiments, which do not limit the scope of the claims. Therefore, the present invention should be only limited by the appended claims. All publications, issued patents, patent applications, books and journal papers cited in the present disclosure are included in the present invention, the entire contents of which are incorporated herein by reference.

The invention claimed is:

1. A method for preventing freezing, comprising adding a compound represented by Formula 1 or Formula 2 below to a solvent:

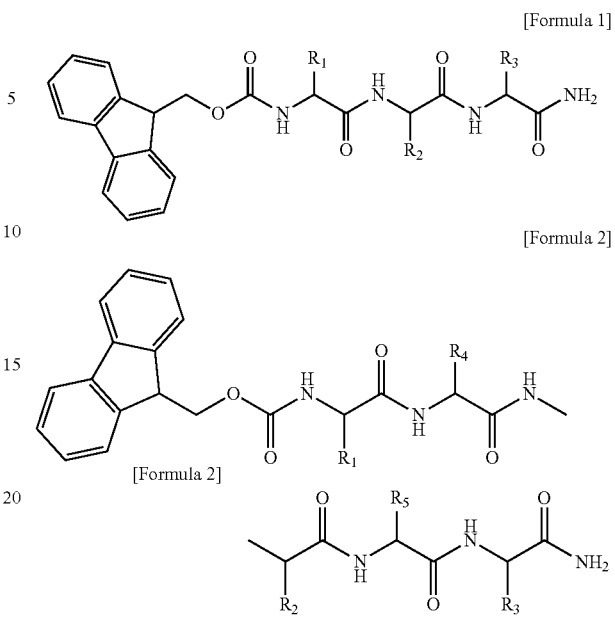

[Formula 1]

[Formula 2]

[Formula 2]

in Formula 1 or 2 above,
$R_1$ and $R_2$ are each independently

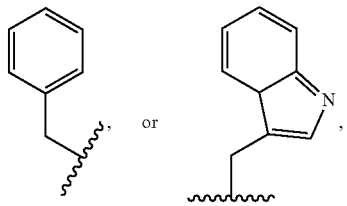 [SMILES: *Cc1ccccc1 ; *CC1=CN=C2C=CC=CC12]

, or , $R_3$ is

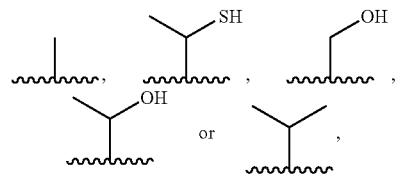

, , , or , and
$R_4$ and $R_5$ are each independently

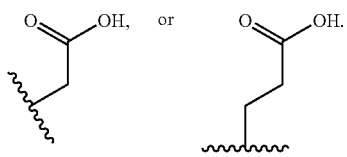

, or .

* * * * *